US012622949B2

(12) United States Patent
Weiss et al.

(10) Patent No.: US 12,622,949 B2
(45) Date of Patent: May 12, 2026

(54) COMPOSITIONS CONTAINING RAPID-ACTING INSULIN ANALOGUES

(71) Applicants: THERMALIN INC., Waban, MA (US); CASE WESTERN RESERVE UNIVERSITY, Cleveland, OH (US)

(72) Inventors: Michael A. Weiss, Indianapolis, IN (US); Mentor Mulaj, North Ridgeville, OH (US); Laurie A. Broadwater, Kent, OH (US); Thomas Hattier, Cleveland Heights, OH (US); Richard Berenson, Waban, MA (US)

(73) Assignees: Case Western Reserve University, Cleveland, OH (US); Invictus Therapeutics, Warwick, RI (US)

( * ) Notice: Subject to any disclaimer, the term of this patent is extended or adjusted under 35 U.S.C. 154(b) by 777 days.

(21) Appl. No.: 17/909,054

(22) PCT Filed: Mar. 2, 2021

(86) PCT No.: PCT/US2021/020491
§ 371 (c)(1),
(2) Date: Sep. 2, 2022

(87) PCT Pub. No.: WO2021/178417
PCT Pub. Date: Sep. 10, 2021

(65) Prior Publication Data
US 2023/0088546 A1      Mar. 23, 2023

Related U.S. Application Data

(60) Provisional application No. 62/984,165, filed on Mar. 2, 2020.

(51) Int. Cl.
| | |
|---|---|
| *A61K 38/28* | (2006.01) |
| *A61K 31/194* | (2006.01) |
| *A61K 31/198* | (2006.01) |
| *A61K 31/5578* | (2006.01) |
| *A61K 33/42* | (2006.01) |
| *A61P 3/10* | (2006.01) |

(52) U.S. Cl.
CPC ............ *A61K 38/28* (2013.01); *A61K 31/194* (2013.01); *A61K 31/198* (2013.01); *A61K 31/5578* (2013.01); *A61K 33/42* (2013.01); *A61P 3/10* (2018.01)

(58) Field of Classification Search
None
See application file for complete search history.

(56) References Cited

FOREIGN PATENT DOCUMENTS

| | | | |
|---|---|---|---|
| WO | 2014015078 | 1/2014 | |
| WO | 2016057529 | 4/2016 | |
| WO | 2016064606 | 4/2016 | |
| WO | 2018094388 | 5/2018 | |
| WO | WO-2018094388 A1 * | 5/2018 | ............ C07K 14/62 |

OTHER PUBLICATIONS

Iloprost CID 5311181 PubChem Entry, dowloaded Aug. 29, 2025 (Year: 2025).*
Berenson, Daniel F. et al, Insulin analogs for the treatment of diabetes mellitus: therapeutic applications of protein engineering, Annals of the New York Academy of Sciences, 2012, pp. E41-E54, vol. 1243, New York Academy of Sciences.

* cited by examiner

*Primary Examiner* — Christina Bradley
(74) *Attorney, Agent, or Firm* — Hahn Loeser & Parks, LLP; John J. Cunniff

(57) ABSTRACT

A pharmaceutical composition comprises an effective amount of an insulin analogue comprising modified A-chain and B-chain polypeptides. The modified A chain comprises one or more substitutions relative to wild-type human insulin A-chain selected from a Gln, His or Glu substitution at position A8, a Glu or Ala substitution at position A14, and an Ala, Gln, Gly, or Thr substitution at position A21. The modified B-chain polypeptide comprises one or more modifications relative to wild-type human insulin B-chain selected from a deletion of the amino acid or amino acids at position B1, B1 and B2, or B1-B3, an Ala or Glu substitution at position B2, a Glu or Ala substitution at position B3, an Ala substitution at position B4; and a Glu or Lys substitution at position B29. The composition comprises one or more of iloprost, citrate, EDTA and a polyphosphate compound. The composition may be used to treat diabetes.

13 Claims, 22 Drawing Sheets
Specification includes a Sequence Listing.

Arginine [ 4.2 mg/mL ] + Iloprost [ 15 ug/mL ] ~

Papaverine [ 12 ug/mL ] ~

Arginine [ 4.2 mg/mL ] ~

Tolazoline [ 10 ug/mL ] ~

GuanidineHCl [ 1.4 mg/mL ] ~

FiveFiveBA [ 200 ug/mL ] ~

Labetalol [ 1 ug/mL ] ~

Arginine [ 8.4 mg/mL ] –
NicotinicAcid [ 100 ug/mL ] –
LidocaineHCl [ 5 mg/mL ] –
Fenoldop [ 0.02 ug/mL ] –
NicotinicAcid [ 30 ug/mL ] –
DiltiazemHCl [ 2.4 ug/mL ] –
CPeptide [ 9.9 nM ] –
SildenafilCitrate [ 0.5 ug/mL ] –
DiltiazemHCl [ 8 ug/mL ] –
Prazosin [ 0.015 ug/mL ] –
ISM [ 0.5 ug/mL ] –

F-1172

F-1154

SEQUENCE LISTING

<160> NUMBER OF SEQ ID NOS: 14

<210> SEQ ID NO 1
<211> LENGTH: 21
<212> TYPE: PRT
<213> ORGANISM: Artificial Sequence
<220> FEATURE:

```
<223> OTHER INFORMATION: SYNTHETIC CONSTRUCT

<400> SEQUENCE: 1

Gly Ile Val Glu Gln Cys Cys Glu Ser Ile Cys Ser Leu Glu Gln Leu
1               5                   10                  15

Glu Asn Tyr Cys Gly
            20

<210> SEQ ID NO 2
<211> LENGTH: 29
<212> TYPE: PRT
<213> ORGANISM: Artificial Sequence
<220> FEATURE:
<223> OTHER INFORMATION: SYNTHETIC CONSTRUCT

<400> SEQUENCE: 2

Ala Glu Gln His Leu Cys Gly Ser His Leu Val Glu Ala Leu Tyr Leu
1               5                   10                  15

Val Cys Gly Glu Arg Gly Phe Phe Tyr Thr Pro Glu Thr
            20                  25

<210> SEQ ID NO 3
<211> LENGTH: 29
<212> TYPE: PRT
<213> ORGANISM: Artificial Sequence
<220> FEATURE:
<223> OTHER INFORMATION: SYNTHETIC CONSTRUCT

<400> SEQUENCE: 3

Ala Ala Gln His Leu Cys Gly Ser His Leu Val Glu Ala Leu Tyr Leu
1               5                   10                  15

Val Cys Gly Glu Arg Gly Phe Phe Tyr Thr Pro Glu Thr
            20                  25

<210> SEQ ID NO 4
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 4

Gly Ile Val Glu Gln Cys Cys Glu Ser Ile Cys Ser Leu Glu Gln Leu
1               5                   10                  15

Glu Asn Tyr Cys Thr
            20

<210> SEQ ID NO 5
<211> LENGTH: 29
<212> TYPE: PRT
<213> ORGANISM: Artificial Sequence
<220> FEATURE:
<223> OTHER INFORMATION: SYNTHETIC CONSTRUCT

<400> SEQUENCE: 5

Ala Glu Gln His Leu Cys Gly Ser His Leu Val Glu Ala Leu Tyr Leu
1               5                   10                  15

Val Cys Gly Glu Arg Gly Phe Phe Tyr Thr Lys Lys Thr
            20                  25

<210> SEQ ID NO 6
<211> LENGTH: 21
<212> TYPE: PRT
<213> ORGANISM: Artificial Sequence
```

-continued

```
<220> FEATURE:
<223> OTHER INFORMATION: SYNTHETIC CONSTRUCT

<400> SEQUENCE: 6

Gly Ile Val Glu Gln Cys Cys Glu Ser Ile Cys Ser Leu Glu Gln Leu
1               5                   10                  15

Glu Asn Tyr Cys Gln
            20

<210> SEQ ID NO 7
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 7

Gly Ile Val Glu Gln Cys Cys Glu Ser Ile Cys Ser Leu Glu Gln Leu
1               5                   10                  15

Glu Asn Tyr Cys Ala
            20

<210> SEQ ID NO 8
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 8

Gly Ile Leu Glu Gln Cys Cys Thr Ser Ile Cys Ser Leu Tyr Gln Leu
1               5                   10                  15

Glu Asn Tyr Cys Asn
            20

<210> SEQ ID NO 9
<211> LENGTH: 29
<212> TYPE: PRT
<213> ORGANISM: Artificial Sequence
<220> FEATURE:
<223> OTHER INFORMATION: SYNTHETIC CONSTRUCT

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Leu
            20                  25

<210> SEQ ID NO 10
<211> LENGTH: 29
<212> TYPE: PRT
<213> ORGANISM: Artificial Sequence
<220> FEATURE:
<223> OTHER INFORMATION: SYNTHETIC CONSTRUCT

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Ala Tyr Thr Pro Leu
            20                  25

<210> SEQ ID NO 11
<211> LENGTH: 29
<212> TYPE: PRT
```

-continued

```
<213> ORGANISM: Artificial Sequence
<220> FEATURE:
<223> OTHER INFORMATION: SYNTHETIC CONSTRUCT

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Gly Tyr Thr Pro Leu
            20                  25

<210> SEQ ID NO 12
<211> LENGTH: 29
<212> TYPE: PRT
<213> ORGANISM: Artificial Sequence
<220> FEATURE:
<223> OTHER INFORMATION: SYNTHETIC CONSTRUCT

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Val Tyr Thr Pro Leu
            20                  25

<210> SEQ ID NO 13
<211> LENGTH: 29
<212> TYPE: PRT
<213> ORGANISM: Artificial Sequence
<220> FEATURE:
<223> OTHER INFORMATION: SYNTHETIC CONSTRUCT

<400> SEQUENCE: 13

Phe Val Asn Gln His Leu Cys Gly Ser His Leu Val Glu Ala Leu Tyr
1               5                   10                  15

Leu Val Cys Gly Glu Arg Gly Phe Leu Tyr Thr Pro Leu
            20                  25

<210> SEQ ID NO 14
<211> LENGTH: 56
<212> TYPE: PRT
<213> ORGANISM: Artificial Sequence
<220> FEATURE:
<223> OTHER INFORMATION: SYNTHETIC CONSTRUCT

<400> SEQUENCE: 14

Phe Val Ala Gln His Leu Cys Gly Ser His Leu Val Glu Ala Leu Tyr
1               5                   10                  15

Leu Val Cys Gly Glu Arg Gly Phe Phe Tyr Thr Pro Leu Glu Glu Glu
            20                  25                  30

Gly Arg Arg Gly Ile Val Glu Gln Cys Cys Glu Ser Ile Cys Ser Leu
        35                  40                  45

Glu Gln Leu Glu Asn Tyr Cys Ala
    50                  55
```

COMPOSITIONS CONTAINING RAPID-ACTING INSULIN ANALOGUES

CROSS REFERENCE TO RELATED APPLICATIONS

This is a national stage application of pending International Application No. PCT/US2021/020491 filed Mar. 2, 2021 which claims benefit of U.S. Provisional Application No. 62/984,165 filed on Mar. 2, 2020, the contents of which are incorporated by reference herein.

STATEMENT REGARDING FEDERALLY SPONSORED RESEARCH OR DEVELOPMENT

This invention was made with government support under grant numbers DK040949 and DK074176 awarded by the National Institutes of Health. The government has certain rights in the invention.

TECHNICAL FIELD

The present invention relates to insulin analogues and compositions thereof with rapid action as well as methods of treating diabetes or methods of managing blood glucose levels in a patient using the insulin analogues or compositions thereof.

BACKGROUND

Insulin has been used for more than 90 years to treat diabetes. Typically, the treatment involves multiple insulin injections every day. According to conventional regimen, patients are treated with one or two daily insulin injections of long-acting insulin to cover the basal insulin requirement supplemented with injections of a fast-acting insulin formulation (or fast-acting insulin analogue formulation) to cover the insulin requirement related to meals. However, even when properly and timely administered, insulin injections do not mimic the natural time-action profile of insulin. For example, commercially available rapid-acting insulin analogues enter into blood and the site of action too slowly and have too long an overall duration of action. This results in inadequate insulin levels at the initiation of a meal and too much insulin present between (and particularly immediately after) meals. In turn, this lag in insulin action causes hyperglycemia early after starting a meal and hypoglycemia after meals.

In healthy individuals, insulin secretion is closely tied to blood glucose level. Increased blood glucose concentration, for example, after meals, is compensated by a rapid increase in insulin release directly into the bloodstream. In the fasting state, insulin levels fall to a basal level. The objective of insulin therapy is to replicate this natural time-action profile of insulin in diabetic patients, such that blood glucose levels can stay within the normal range characteristic of healthy individuals. However, current insulin products and delivery systems do not sufficiently meet this objective due to limitations in the absorption of the insulin or insulin analogue.

For example, insulin formulations (or insulin analogue formulations) containing a predominance of protein molecules in the forms of monomers (which is the predominant form of insulin circulating in blood) and dimers have a strong tendency to aggregate and form inactive fibrils. For example, when insulin is solubilized in a buffer without zinc and stored at room temperature (25-30° C.), the insulin will form amyloid fibrils. To avoid this problem, currently available insulin products are typically formulated with zinc, which forms a complex with insulin called a zinc-insulin hexamer. Zinc-insulin hexamers can be stable in solution at room temperature for greater than 30 days, which is long enough to meet regulatory requirements for insulin formulation stability. However, zinc-insulin hexamers are too large to be readily absorbed by capillaries, and so the hexamers must disassemble in the subcutaneous interstitial fluid after injection before the insulin can be absorbed into the circulation. The hexameric formulation required for stabilization of the insulin in the vial prevents these formulations from being absorbed quickly enough to match physiological insulin secretion.

Accordingly, rapid acting insulin analogues and compositions thereof are needed for better management of blood glucose levels in diabetic patients.

SUMMARY OF THE INVENTION

The present invention relates, in part, to insulin analogues or pharmaceutically acceptable compositions thereof that provide for rapid uptake of the analogue into the blood resulting in its rapid onset of action, for example, as compared to existing commercial insulin products and other similar insulin analogues. Further, in various embodiments, the insulin analogues and compositions have advantages in stability (e.g. as quantified by the rate of fibril formation, change in chemical stability after 7 and 28 days, and change in physical stability after 7 and 28 days), and mitogenicity (e.g. as quantified in cell-based proliferation assays). Formulation of the analogues with optimized selection and concentrations of excipients enhances the analogues' pharmacologic and thermodynamic stability advantages. Accordingly, in some embodiments, the present invention provides insulin analogues or pharmaceutically acceptable compositions thereof that exhibit a more rapid onset of insulin action (as compared to commercial insulin analogues or wild-type human insulin) without a decrease in stability (as compared to commercial insulin analogues or wild-type human insulin).

In one aspect, the present invention provides a pharmaceutical composition comprising an effective amount of an insulin analogue comprising modified A-chain B-chain polypeptides. The modified A chain comprises one or more substitutions relative to the wild-type human insulin A-chain selected from a Gln, His or Glu substitution at position A8, a Glu or Ala substitution at position A14, and an Ala, Gln, Gly, or Thr substitution at position A21. The modified B-chain polypeptide comprises one or more modifications relative to the wild-type human insulin B-chain selected from a deletion of the amino acid or amino acids at position B1, positions B1 and B2, or positions B1-B3, an Ala or Glu substitution at position B2, a Glu or Ala substitution at position B3, an Ala substitution at position B4; and a Glu or Lys substitution at position B29. The composition also comprises one or more of iloprost, citrate, EDTA and a polyphosphate compound. The pharmaceutical composition may be formulated for use in the treatment of diabetes mellitus.

In another aspect, the present invention provides an insulin analogue comprising a modified A-chain polypeptide and a modified B-chain polypeptide. For example, the A chain comprises or consists of substitutions relative to the wild-type human insulin (HI) A-chain selected from: a Glu substitution at position A8; a Glu substitution at position A14; and a Gly substitution at position A21. Further, the B-chain polypeptide will comprises or consists of modifications relative to the wild-type human insulin B-chain selected from: a deletion of the residue at position B1, an Ala or Glu substitution at position B2 or B3; and a Glu substitution at position B29.

In some embodiments, the modified A-chain polypeptide comprises a Gly substitution at position A21. In some embodiments, the modified B-chain polypeptide comprises a Glu substitution at position B3. In some embodiments, the modified A-chain polypeptide comprises an Ala substitution at position A21. In some embodiments, the modified B-chain polypeptide comprises an Ala substitution at position B3. In one embodiment, an analogue is referred to as T-1123, has the following modifications: GluA8, GluA14, GlyA21, desB1, AlaB2, GluB3, and GluB29.

Another aspect of the present invention provides a pharmaceutical composition comprising an effective amount of the insulin analogue and excipients to enhance the insulin analogue's pharmacologic and thermodynamic stability advantages. For example, the formulation may comprise, but is not limited to, tonicity agents, preservatives, stabilizing agents, solubilizing agents, or absorption enhancing agents. In some embodiments, the pharmaceutical composition comprises an effective amount of the rapid acting insulin analogue and a polyphosphate compound (e.g., sodium triphosphate). In some embodiments, the pharmaceutical composition comprises an effective amount of the rapid acting insulin analogue and iloprost.

Yet another aspect of the present invention provides a method for treating a subject with diabetes, comprising administering the insulin analogue or the pharmaceutical composition of the present disclosure to a subject in need thereof.

Yet another aspect of the invention provides a method for determining pharmacokinetic (PK) parameters or profile of an active pharmaceutical ingredient (API) formulation. This method includes administering multiple inactive or non-potent analogue (nonalog) compositions of the API to a test subject or a first test subject and determining concentration of the nonalogs in one or more tissue samples from the test subject or the first subject. The method also includes determining one or more pharmacokinetic parameters for the API formulation based on the concentration of the nonalogs in the test subject or the first subject. In one embodiment, this method is used to determine PK parameters for a nonalog and use it as a proxy for determining the PK parameters for the corresponding API. In some embodiments, the nonalogs are non-potent analogues of a peptide hormone, such as insulin.

In some embodiments, the invention provides a method for making a pharmaceutical formulation of an API. This method includes administering to a test subject multiple nonalog compositions of the API and determining the concentrations of the nonalogs in one or more samples from the test subject. The method also includes determining pharmacokinetic profiles for the nonalog compositions and formulating the API as a pharmaceutical formulation utilizing an analogous composition to achieve the desired pharmacokinetic profile. In one embodiment, the method further includes determining the desired pharmacokinetic profile based on the concentrations of the nonalogs in one or more samples from the test subject. Once a desired pharmacokinetic profile or parameter for the nonalog composition is achieved, then, this API can be formulated such that it mimics the nonalog composition, except, that the nonalog in the selected nonalog composition is replaced with the corresponding API.

In another aspect, the invention is related to a non-potent analogue (nonalog) composition. This composition includes a nonalog of an API and a pharmaceutically acceptable carrier. This nonalog composition is used in determining pharmacokinetic parameters of the corresponding API or a pharmaceutical formulation for the corresponding API.

The present invention in various aspects provides methods for increasing the efficiency of PK formulation studies. Since administering multiple substantially simultaneous clinically-relevant doses of an API would create a much higher concentration of the API in the subject's bloodstream than would be used for normal treatment (and thus would present potential safety issues, and lead to morbidity or mortality of the test subjects), the invention provides for the use of non-potent or inactive analogues (nonalogs). The methods and products described herein allow for the evaluation of PK of potential API formulations without subjecting multiple subjects to stress, while minimizing cost.

Other aspects and embodiments of the invention will be apparent from the following detailed description.

BRIEF DESCRIPTION OF THE DRAWINGS

FIG. 6A is minus citrate; FIG. 6B is minus EDTA; and FIG. 6C is minus iloprost.

Figure 7A:
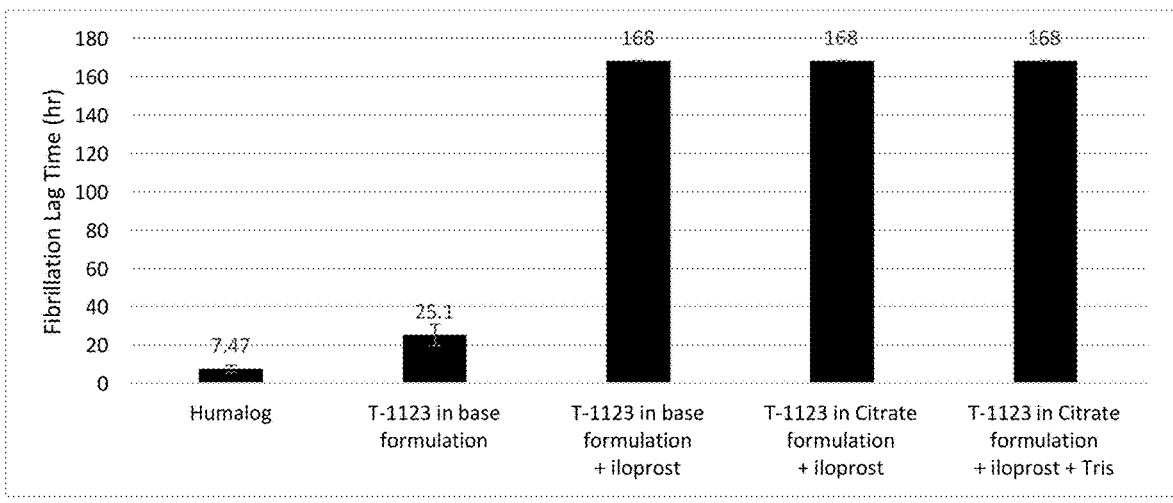
FIG. 7A shows the results obtained from an accelerated fibrillation assay showing mean fibrillation lag times for Humalog (n=6), T-1123 in base formulation (n=11), T-1123 in base formulation+iloprost (n=3), T-1123 in citrate formulation+iloprost (n=6), and T-1123 in citrate formulation+iloprost+Tris (n=15). Base formulation for U-500 T-1123 is 16 mg/mL glycerin, 3.2 mg/mL m-cresol, and 50 mM Tris.
Figure 7B:
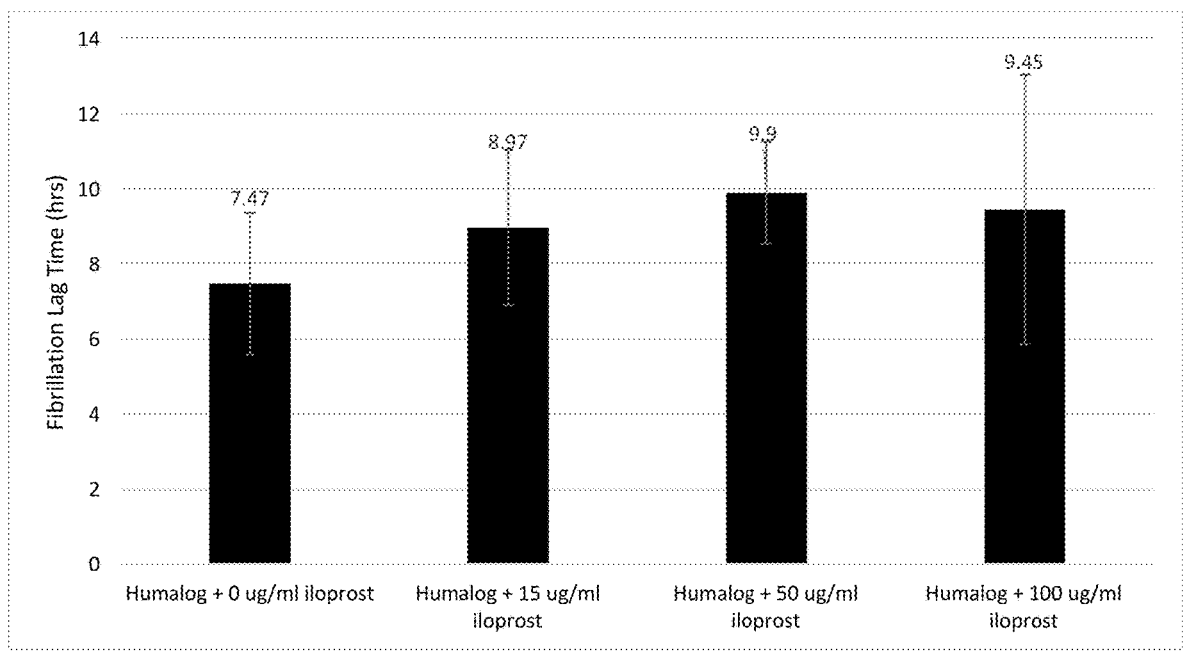

FIG. 7B shows the results obtained from an accelerated fibrillation assay showing mean fibrillation lag times for Humalog formulated with no iloprost (n=3), 15 μg/ml iloprost (n=3), 50 μg/ml iloprost, and 100 μg/ml iloprost (n=3).

Figure 7C:
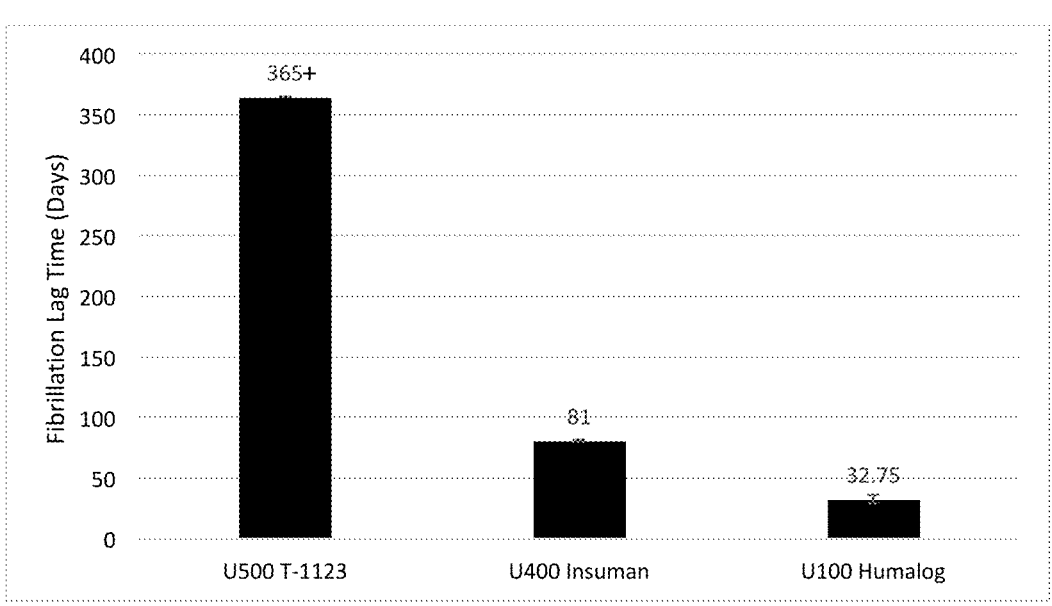

FIG. 7C shows the results obtained from a 12 month real time fibrillation assay showing mean fibrillation lag times for U-500 T-1123 in accelerated formulation optimized for stability, U-400 Insuman, and U-100 Humalog. All samples were placed in vials, then placed on a nutator at 30° C. for 1 year. N=3 for all samples. Fibrillation lag time is measured in days.

Figure 8A:
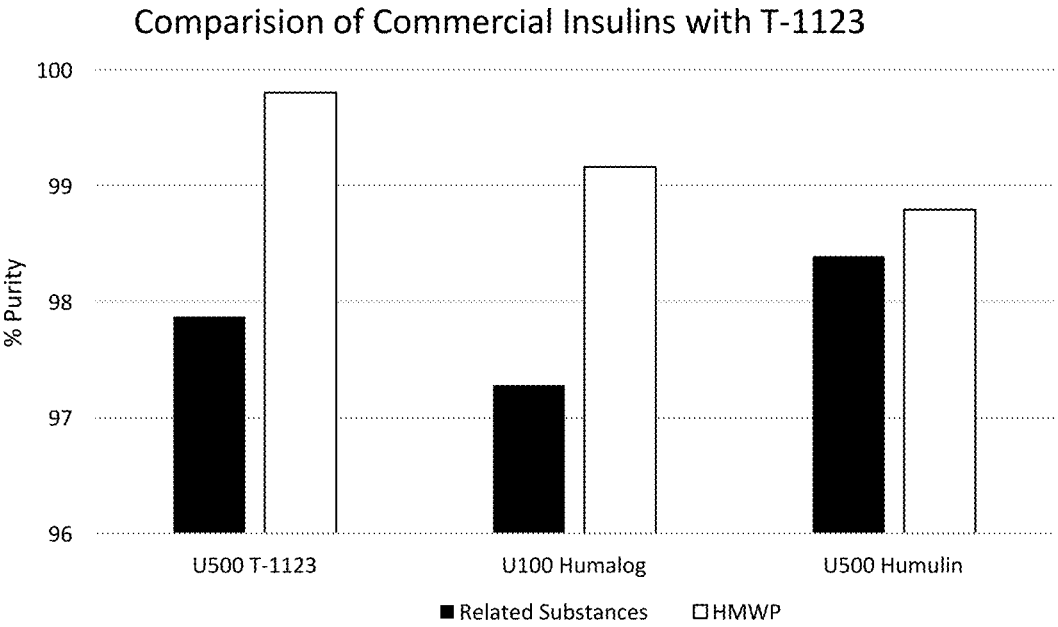

FIG. 8A shows the results obtained from chemical degradation studies showing losses in purity due to accumulation of Related Substances (RS) and covalent High Molecular Weight Protein (HMWP) for U-500 T-1123 in a base formulation (n=1), commercial U-100 Humalog (n=2), and commercial U-500 Humulin (n=2).

Figure 8B:
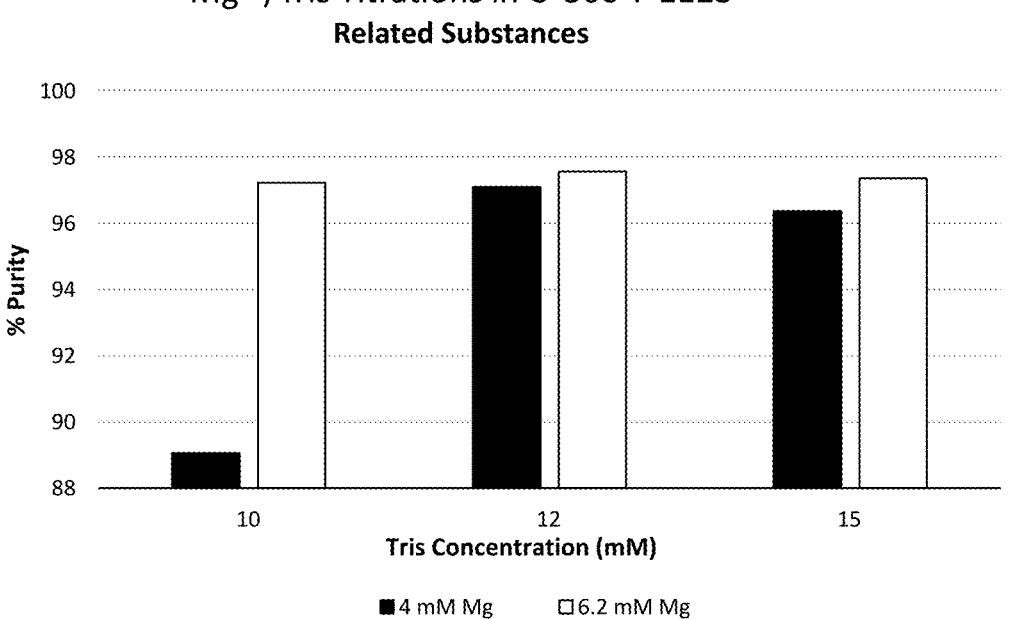

FIG. 8B shows the results obtained from a chemical degradation assay to evaluate accumulation of related substances for a formulations of U-500 T-1123 in which $Mg^{2+}$ and Tris concentrations were varied.

Figure 8C:
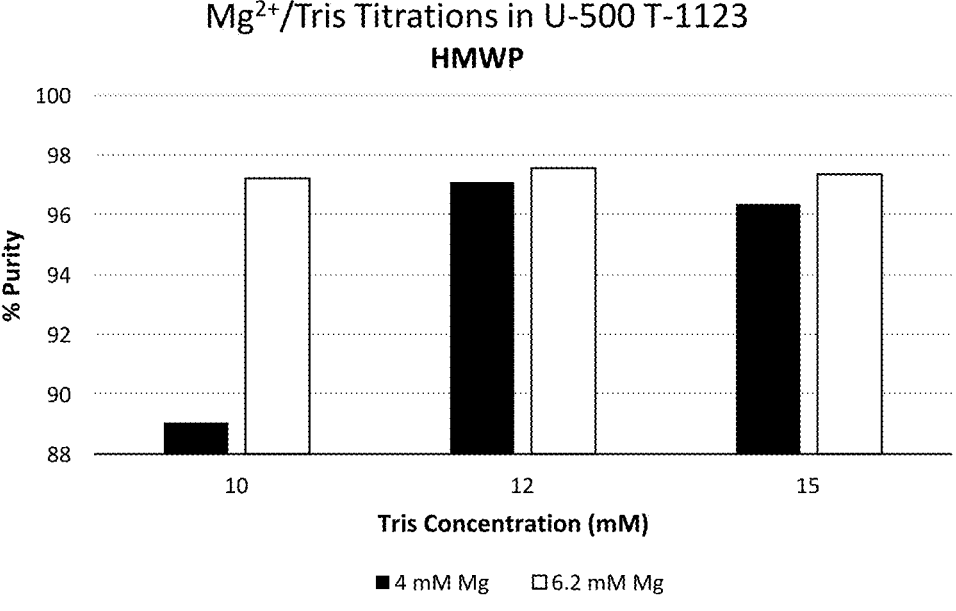

FIG. 8C shows the results obtained from a chemical degradation assay to evaluate accumulation of HMWP for formulations of U-500 T-1123 in which $Mg^{2+}$ and Tris concentrations were varied.

Figure 8D:
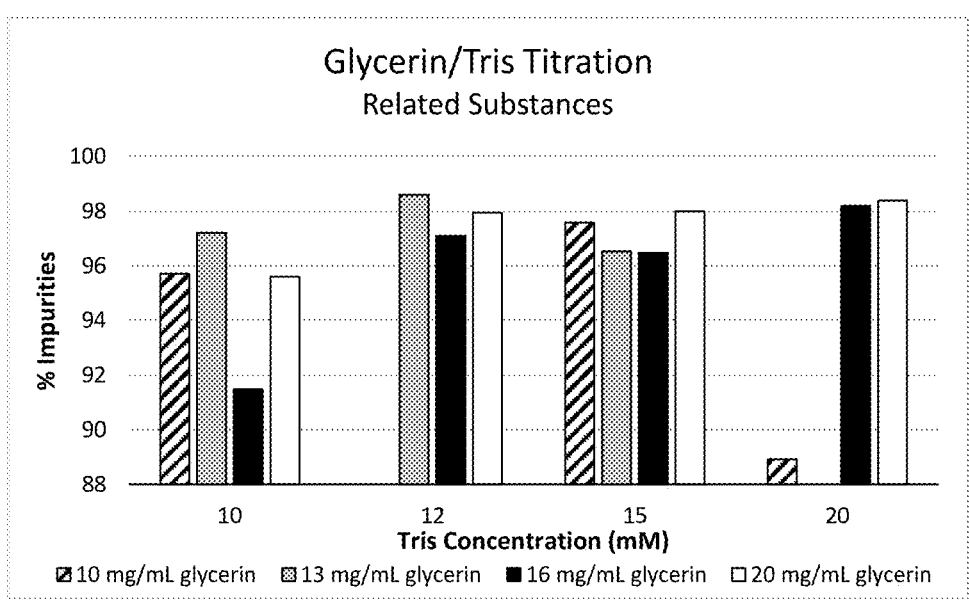

FIG. 8D shows the results obtained from a chemical degradation assay to evaluate accumulation of RS for formulations of U-500 T-1123 in which glycerin and Tris concentrations were varied.

Figure 8E:
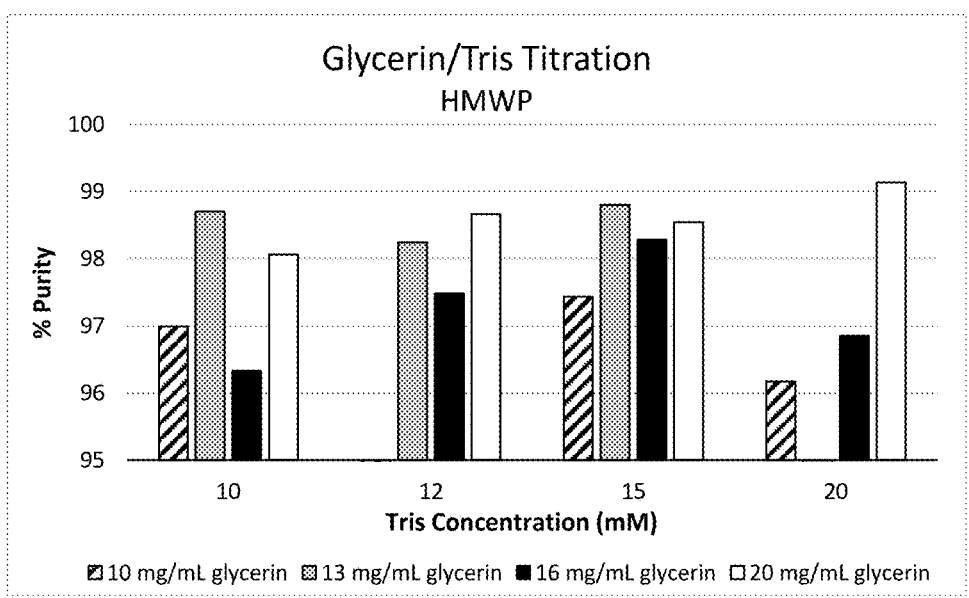

FIG. 8E shows the results obtained from a chemical degradation assay to evaluate accumulation of HMWP for formulations of U-500 T-1123 in which glycerin and Tris concentrations were varied.

Figure 8F:
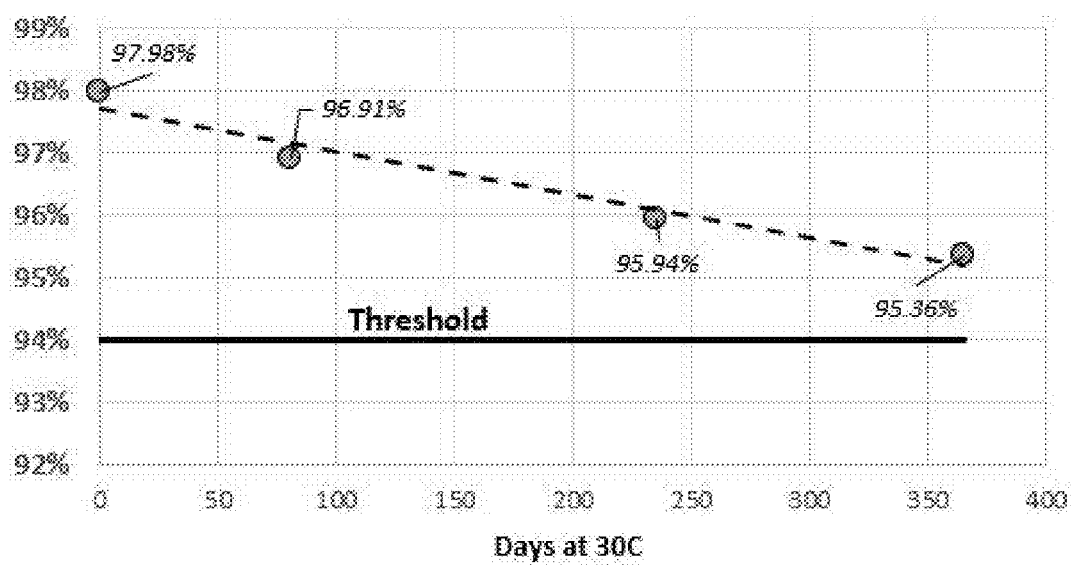

FIG. 8F shows the results obtained from a chemical degradation assay to evaluate Related Substances purity for U-500 T-1123 placed in vials, then placed on a nutator at 30° C. for 1 year.

Figure 8G:
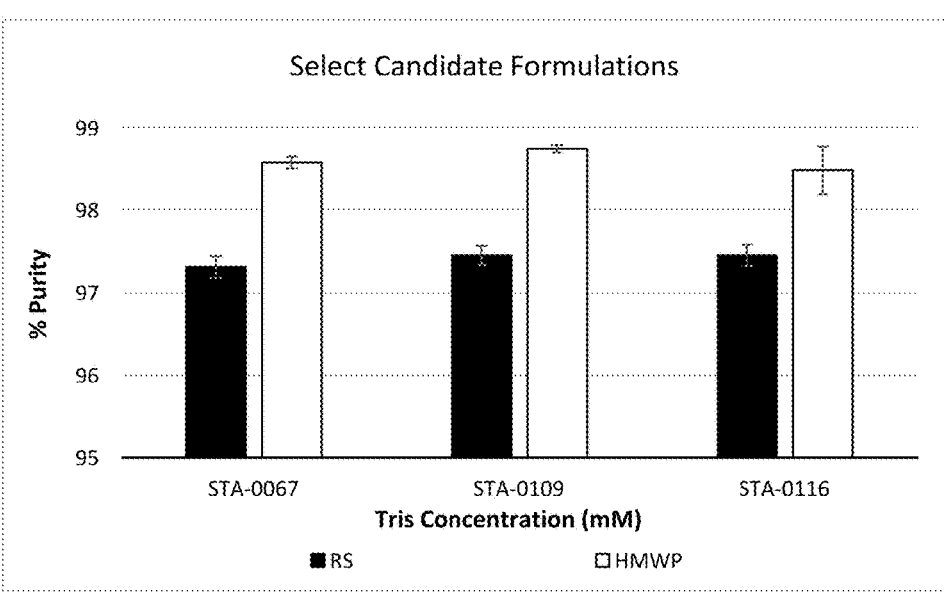

FIG. 8G shows the results obtained from a chemical degradation assay to evaluate Related Substances purity for U-500 T-1123 placed in vials, then placed on a nutator at 30° C. for 1 year.

Figure 9A:
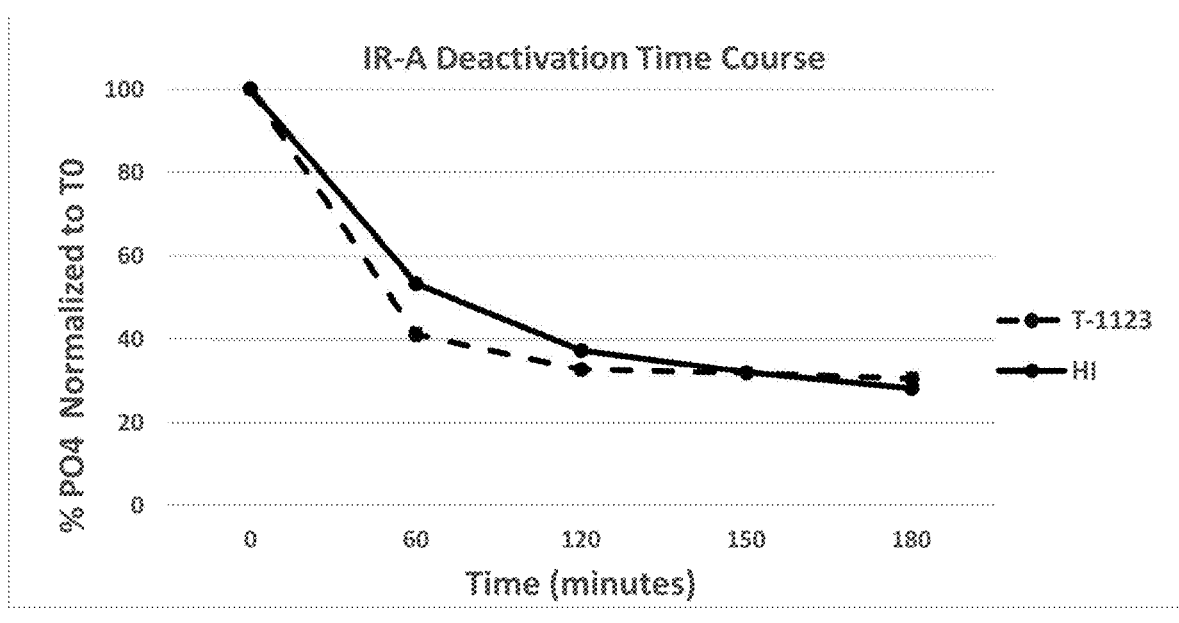

FIG. 9A shows the results obtained from an in-cell western blot assay measuring dephosphorylation of hIR-A in CHO cells over 180 minutes after treatment with either HI (n=1) or T-1123 (n=3).

Figure 9B:
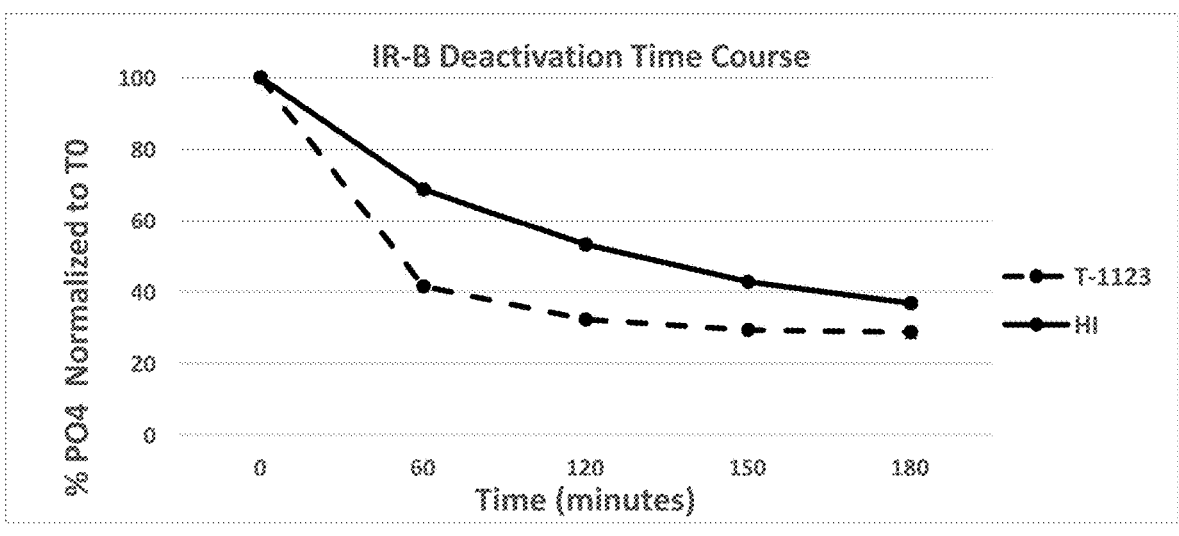

FIG. 9B shows the results obtained from an in-cell western blot assay measuring dephosphorylation of hIR-B in CHO cells over 180 minutes after treatment with either HI (n=1) or T-1123 (n=2).

Figure 10A:
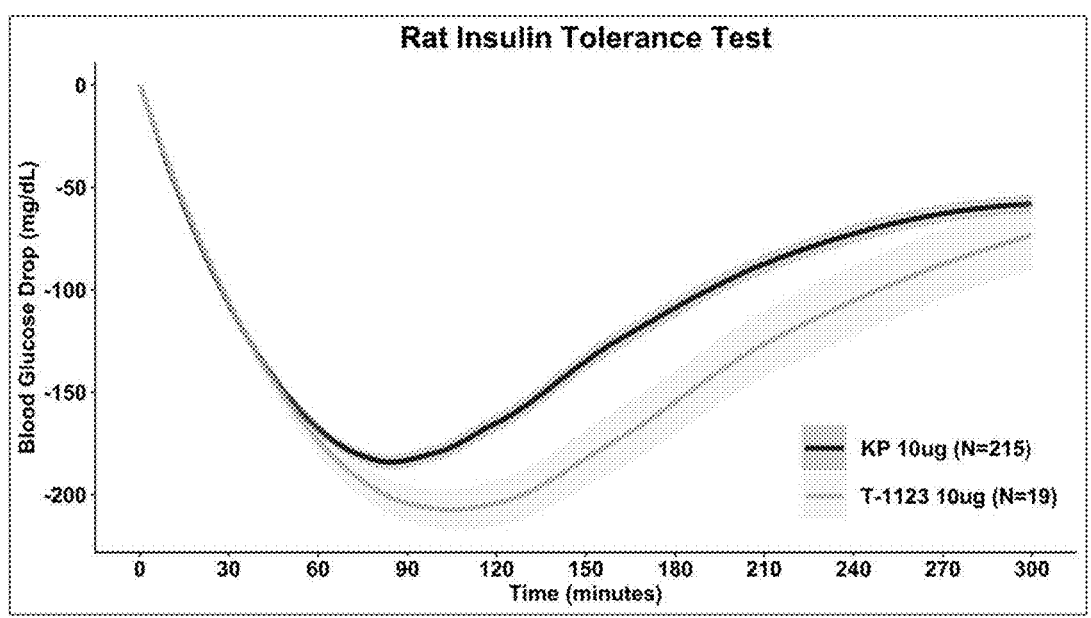

FIG. 10A shows the results obtained from monitoring rats for change in blood glucose concentrations over 300 minutes when treated with either insulin lispro (KP) (n=215) or T-1123 (n=19).

Figure 10B:
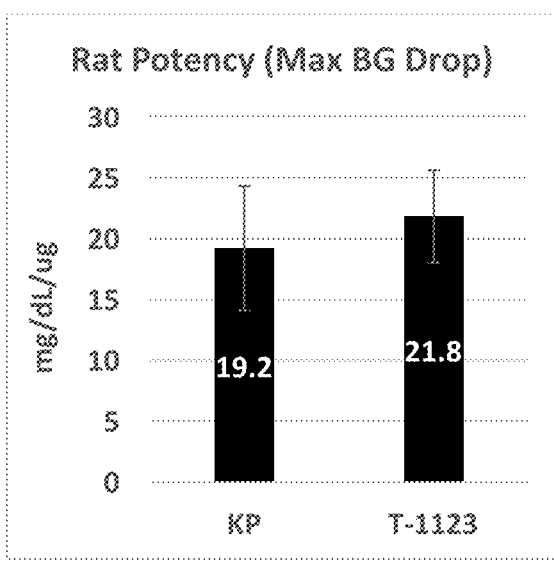
Figure 10B:
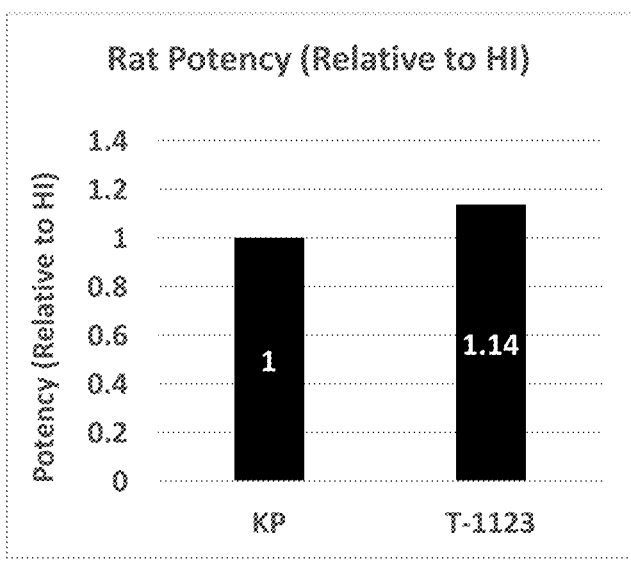

FIG. 10B shows the results obtained from rat studies showing maximum blood glucose drop (Max BG Drop) when the animals were treated with either insulin lispro (KP) (N=215) or T-1123 (n=19).

Figure 11A:
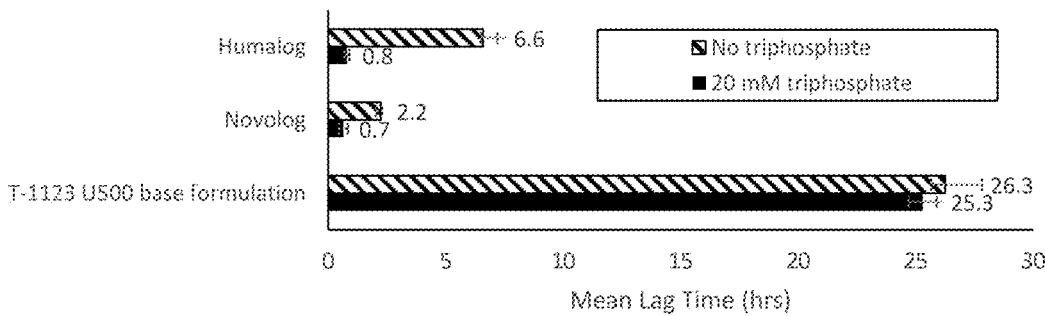

FIG. 11A shows the results obtained from an accelerated fibrillation assay showing mean fibrillation lag times (n=3) for Humalog® (with or without triphosphate), Novolog® (with or without triphosphate) and T-1123 (formulated at U-500 with or without triphosphate).

Figure 11B:
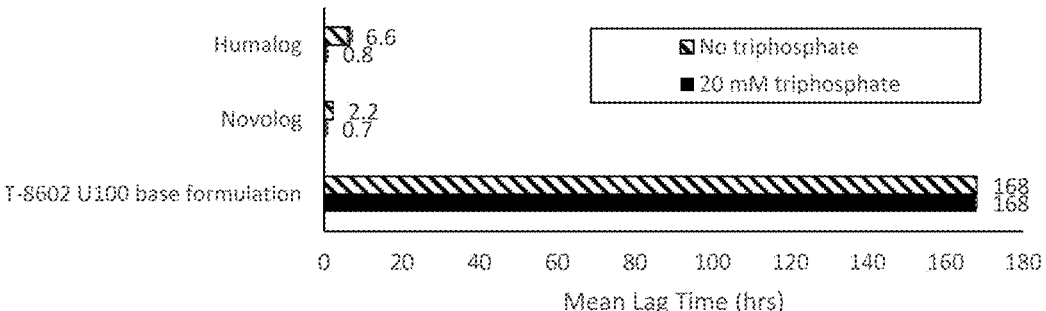

FIG. 11B shows the results obtained from an accelerated fibrillation assay showing mean fibrillation lag times (n=3) for Humalog® (with or without triphosphate), Novolog® (with or without triphosphate) and T-8602 (formulated at U-100 with or without triphosphate). T-8602 is a single chain insulin analogue having the following modifications: EA8, EA14, AA21, AB3, EB29, and an EEGRR linker connecting the B30 and A1 positions.

Figure 11C:
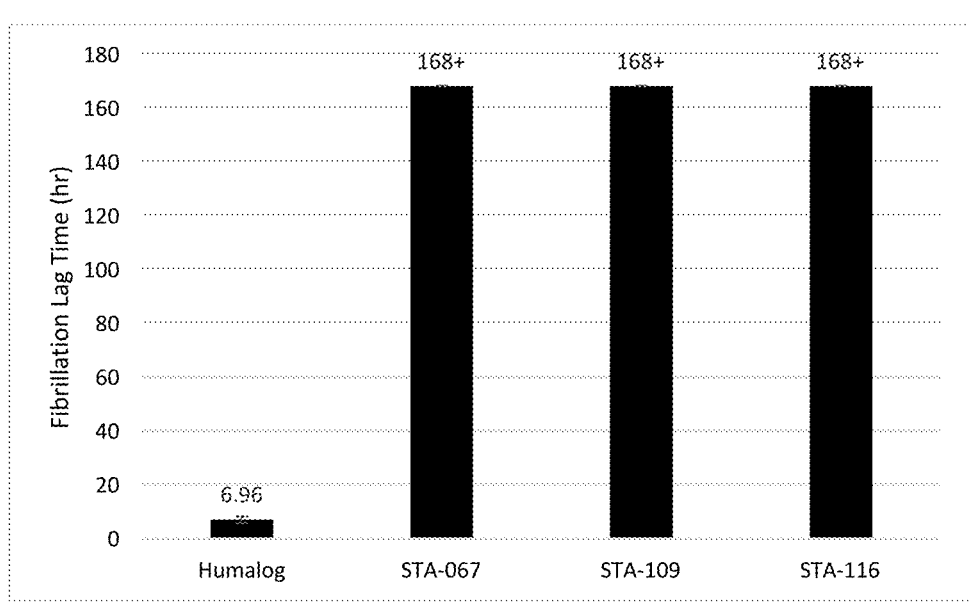

FIG. 11C shows the results obtained from an accelerated fibrillation assay, showing mean fibrillation lag times for Humalog (n=3) and T-1123 in 3 different formulations: STA-067 (n=3), STA-109 (n=3), and STA-116 (n=3).

Figure 12:
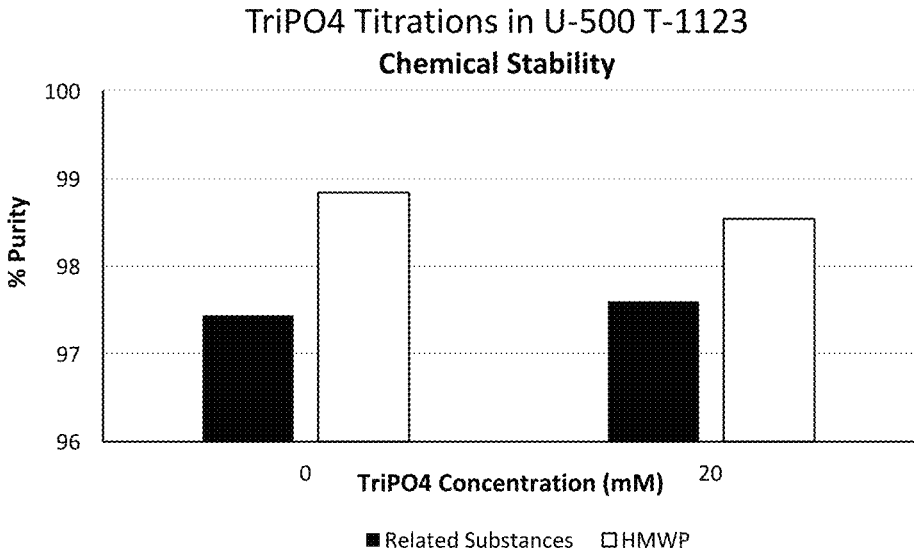

FIG. 12 shows the results obtained for RS and HMWP following a forced chemical degradation assay on U-500 T-1123 base formulations in the absence and presence of TriPO4.

DEFINITIONS

The terms "formulation" and "composition" are used interchangeably herein. The term "formulation" or "composition" as used herein encompasses the chemical substances or excipients added to the active pharmaceutical ingredient (API) in order to, e.g., confer or support desired pharmacological properties to the API. These properties may include, but are not limited to, rapid absorption, delayed absorption, extended release, extended half-life, reduced clearance rate, increased clearance rate, and charge masking. The term "formulation" also encompasses the relative concentrations of the API or nonalog in the composition, as well as the underlying carrier (e.g., aqueous solution, solid powder in a capsule, coatings on the capsule, and so on).

The term "subject" or "patient" as used herein is intended to encompass human patients and non-human animals, e.g., those used in preclinical testing, such as, mice, rats, rabbits, dogs, pigs, cats, primates, and cattle.

The term "thermodynamic stability" as used herein is intended to encompass physical and chemical stability as measured by self-assembly of either amorphous aggregates, or insoluble highly-structured fibrillar species, as well as loss of purity of the insulin analogue composition due to accumulation of covalent high molecular weight protein (HMWP) or related substances (RS), respectively.

As used herein, the term "Active Pharmaceutical Ingredient (API)" is a substance or mixture of substances intended to be used in the manufacture of a drug (e.g., a medicinal) product and that, when used in the production of a drug, becomes an active ingredient of the drug product. Such substances are intended to furnish pharmacological activity or other direct effect in the diagnosis, cure, mitigation, treatment, or prevention of disease or to affect the structure or function of the body. APIs include a drug substance for use in diagnosis, cure, mitigation, treatment, or prevention of a disease. An API can be, for instance, a protein, a peptide, a small molecule, an oligonucleotide, or a polymer. An API can be an insulin analog. The term "drug product" as used herein is a finished dosage form, for example, a tablet, capsule or solution that contains an active pharmaceutical ingredient, generally, but not necessarily, in association with inactive ingredients. The term is intended to encompass the final dosage form of an API combined with various pharmaceutically acceptable carriers or excipients that make an API formulation.

The term "administration" as used herein is intended to encompass a method whereby an API, a drug product or a nonalog is introduced into a test subject's body. Exemplary routes of administration include, but are not limited to, oral, subcutaneous, sublingual, intramuscular, intravenous, intradermal, intraperitoneal, buccal, or nasal.

The term "nonalog" as used herein is intended to encompass inactive or non-potent analogues of an API. These nonalogs have a similar chemical structure, primary structure, secondary structure, tertiary structure, quaternary structure, hydrophobicity structure, or similar surface charge pattern to the API. In some instances, the nonalog is sufficiently distinct from other nonalogs of the API so that it can be reliably detected and/or separated from the other nonalogs in a sample, yet sufficiently similar that the PK properties of the nonalog are not expected to differ significantly from the corresponding API. In a non-limiting example, different nonalogs of an API could differ from each other by mass. The terms "tissue sample" or "sample" as used herein is intended to encompass samples of solid, liquid, and gaseous extracts taken from a subject, including without limitation biopsy samples, blood, urine, and spinal fluid samples, and exhalate samples.

As used herein, unless otherwise required by the context, the term "about" means+ or −10% of the associated numerical value

DETAILED DESCRIPTION

Insulin has the ability to self-associate into dimers, hexamers, high molecular weight aggregates, and insoluble fibrils (at therapeutic concentrations). Loss of purity via formation of related substances, high molecular weight covalent and non-covalent protein aggregates, or insoluble amyloid fibrils is a problem in the treatment of diabetes, especially in the context of pharmaceutical compositions that are intended to be stored before use. During the fibrillation process, several kinds of conformational changes may occur in the insulin structure. Insulin is thought to form either an amyloid-like structure or amorphous aggregates at the stage preceding fibrillation. These amyloid fibrils are rich in β-sheet conformations. Unrelated to native assembly, fibrillation is believed to occur via an amyloidogenic partial fold. Zinc-free insulin is especially susceptible to loss of purity under a broad range of conditions and is thought to be promoted by factors that impair native dimerization and higher-order self-assembly. The storage form of insulin in the pancreatic β-cell and in the majority of pharmaceutical formulations is stabilized by axial zinc (Zn) ions coordinated by the side chains of insulin amino acids, specifically the HisB10 residues. Formulation of insulin or insulin analogues as a zinc-stabilized hexamer retards but does not prevent fibrillation, especially above room temperature and on agitation. Storage of insulin analogues as zinc-stabilized hexamers has the additional drawback of delaying the action of the analogue, since insulin needs to dissociate into monomers to bind to the insulin receptor. This is particularly an obstacle in the creation of rapid-acting insulin analogues, which must overcome either the stability problems exhibited by monomeric, Zn-free formulations or the delayed action exhibited by hexameric formulations.

The present invention in various aspects and embodiments is directed toward a rapid-acting insulin analogue, as well as formulations that provides rapid action under a broad range of protein concentrations and formulation strengths (typically from U-100 to U-500, and optionally as high as U-1000). In various embodiments, the mitogenicity of the insulin analogue is no greater than that of insulin lispro (abbreviated as KP, a commercially available rapid-acting insulin analogue). In various embodiments, the thermodynamic stability of the insulin analogue or composition thereof in the absence of zinc ions is equal to or greater than that of commercially available insulin analogues formulated in the presence or absence of zinc ions.

The present invention provides for insulin analogues or compositions thereof that, in some embodiments, do not form fibrils or exhibit delayed fibril formation or exhibit an increase in fibrillation lag time. In some embodiments, the insulin analogues or compositions thereof exhibit high physical and chemical stability in the form of minimal loss of purity due to accumulation of HMWP and RS. The invention further provides for insulin compositions that include various excipient compounds providing high levels of thermodynamic stability and a high rate of absorption of the insulin analogue.

In some embodiments, the insulin analogues or compositions thereof do not form insulin fibrils or take much longer to form insulin fibrils as compared to, e.g., wild-type human insulin or commercial insulin analogue formulations. In some embodiments, the insulin analogues or compositions thereof exhibit increased thermodynamic stability as compared to, e.g., wild-type human insulin or commercial insulin analogue formulations. In embodiments, the insulin analogue compositions described herein provide the ability to store the composition for a longer duration without unwanted fibril formation and/or without unwanted physical or chemical degradation or aggregation. Methods of using the insulin and insulin analogue compositions for treating subjects with diabetes (e.g., for managing blood glucose levels) are also provided.

In accordance with embodiments of the present invention, formulations of rapid-acting insulin analogues are provided having excipients that provide unexpectedly superior pharmacodynamic properties and/or unexpectedly superior properties in physical and/or chemical stability. In various embodiments, this disclosure provides a comprehensive comparative evaluation of the effectiveness of various insulin analogue formulation components. These studies identify component formulations that meet the stability and absorption-speed requirements for an improved human therapy. In accordance with embodiments of the invention, insulin analogues and formulations are provided that better replicate the natural time-action profile of insulin without forming undesirable fibrils during storage.

Superior properties of the invention are partially conferred by a novel combination of substitutions within the A and B chains of the insulin analogue, paired with an N-terminal deletion of the B chain. The A- and B-chain substitutions fall into four classes: (i) non-beta-branched substitutions at position A8; (ii) helicogenic substitutions at position A14 containing side chains that are either polar, charged or smaller than the native tyrosine; (iii) substitutions at positions B28 and/or B29 to decrease dimerization of insulin or to enhance its solubility at neutral pH; and (iv) substitutions near the N-terminus of the B chain in conjunction with N-terminal deletions. Some of these substitutions may in isolation augment the stability of wild-type insulin whereas others may in isolation impair the stability of wild-type insulin. Likewise, some of these substitutions may in isolation extend the tail of insulin action (on intravenous bolus injection) whereas others may in isolation mitigate or foreshorten this tail. An aspect of the invention provides a combination of such substitutions, in conjunction with N-terminal deletion of the B-chain, which together provide an insulin analogue whose formulation under a broad range of protein concentrations in the range 0.6-12.0 mM retains rapid action on subcutaneous injection and exhibits adequate physical and chemical stability to be practical for the treatment of diabetes mellitus.

In some aspects, the insulin analogues of the present invention are two-chain insulin analogues that contain a modified A-chain polypeptide and a modified B-chain polypeptide. See, e.g., WO 2018/094388, which is hereby incorporated by reference in its entirety. In some embodiments, the insulin analogue of the present invention comprises or consists of the following modifications with respect to wild type human insulin: EA8, EA14, GA21, desB1, AB2, EB3, and EB29.

In one embodiment, the insulin analogue of the present invention comprises a modified A-chain having the following amino acid sequence:

(SEQ ID NO: 1)
GIVEQCCESICSLEQLENYCG

In one embodiment, the insulin analogue of the present invention comprises a modified B-chain having the following amino acid sequence:

(SEQ ID NO: 2)
AEQHLCGSHLVEALYLVCGERGFFYTPET

In various embodiments, the insulin analogue of the present invention is a monomeric insulin analogue or dimeric insulin analogue. As used herein, a "monomeric insulin analogue" refers to an insulin that is stable for at least 30 days at 25° C. when it is formulated substantially without zinc (e.g., less than about 0.05 moles of zinc per mole of insulin) and thus present in solution predominately in a monomeric and/or dimeric form as opposed to the zinc-hexameric form. For example, the monomeric insulin analogue can be formulated at a high concentration, such as at 100 IU/ml (e.g., about U-100) or greater (e.g., about U-200, about U-300, about U-400, about U-500, about U-1000, about U-1500, or about U-2000) without significant fibril formation or chemical degradation. In some embodiments, the insulin analogue is formulated at about U-100 to about U-1000, or at about U-100 to about U-500. In various embodiments, the monomeric insulin is stable in the pharmaceutical composition for at least about 1 month, or at least about 2 months, or at least about 3 months, or at least about 4 months, or at least about 5 months, or at least about 6 months, or at least about 9 months, or at least about 12 months at 25° C. without substantial formation of insulin fibrils (i.e., less than 1 percent fibril formation).

In some embodiments, the insulin analogues and compositions thereof have higher stability as compared to wild-type insulin, insulin lispro or insulin aspart in zinc-free or zinc-containing formulations. In various embodiments, the insulin analogue or compositions thereof exhibit a lower rate of fibrillation as compared to Humalog® (Eli Lilly & Co., Indianapolis, Ind.), Novolog®, (Novo Nordisk, Bagsværd, Denmark) or wild-type human insulin. In various embodiments, the insulin analogue or compositions thereof exhibit a lower rate of degradation into HMWP as compared to Humalog®, Novolog®, or wild-type human insulin. In various embodiments, the insulin analogue or compositions thereof exhibit a lower rate of degradation into RS as compared to Humalog®, Novolog®, or wild-type human insulin.

In various embodiments, the insulin analogue or compositions thereof exhibit a lower rate of fibrillation as compared to Humalog®, Novolog®, or wild-type human insulin in a concentrated formulation of U-500. In various embodiments, the insulin analogue or compositions thereof exhibit a lower rate of degradation into HMWP as compared to Humalog®, Novolog®, or wild-type human insulin in a concentrated formulation of U-500. In various embodiments, the insulin analogue or compositions thereof exhibit a lower rate of degradation into RS as compared to Humalog®, Novolog®, or wild-type human insulin in a concentrated formulation of U-500.

In various aspects and embodiments, the present invention provides a pharmaceutical composition and/or formulation that comprises an effective amount of the insulin analogues as described herein and a polyphosphate compound. In some embodiments, the formulation is at least U-100 or at least U-500. Polyphosphates are salts or esters of polymeric oxyanions formed from tetrahedral $PO_4$ (phosphate) structural units linked together by sharing oxygen atoms. In some embodiments, the polyphosphate compounds are incorporated in the compositions of the present invention at an amount effective to increase the rate of absorption of the insulin analogue upon administration. In various embodiments, the polyphosphate is selected from one or more of a pyrophosphate, a triphosphate, a trimetaphosphate, and tetraphosphate. The polyphosphate may be used in their acidic form or in various salt forms, e.g., as alkali (e.g., sodium or potassium) salts or alkaline metal (e.g., calcium and magnesium) salts. In some embodiments, the polyphosphate comprises sodium triphosphate.

The concentration of polyphosphates (e.g., sodium triphosphate) in the composition is from about 1 mM to about 100 mM, or from about 1 mM to about 50 mM, or from about 1 mM to about 40 mM, or from about 5 mM to about 50 M. In some embodiments, the concentration of polyphosphate in the composition is about 5 mM, about 10 mM, about 15 mM, about 20 mM, about 25 mM, about 30 mM, about 35 mM, about 40 mM, about 45 mM or about 50 mM. In some embodiments, the concentration of polyphosphate in the composition is from about 10 mM to about 100 mM, or from about 10 mM to about 50 mM. In some embodiments, the concentration of the polyphosphate in the composition is from about 15 mM to about 35 mM. In some embodiments, the concentration of the polyphosphate is from about 10 mM to about 30 mM. In some embodiments, the concentration of the polyphosphate is about 20 mM, where the polyphosphate is optionally sodium triphosphate. In some embodiments, fibrillation of insulin or its analogue can be evaluated by using Thioflavin T (ThT) dye assay. Thioflavin T dye is highly sensitive to the construction of fibrils. ThT dye interacts with amyloid fibrils without changing the structure or sequence of the proteins. See, Wang J.-B., Wang Y.-M., Zeng C.-M., Biochem. Biophys. Res. Commun. 2011, 415, 675-679, which is hereby incorporated by reference in its entirety. The dye has emission and excitation bands at $\lambda$=480 nm and 440 nm, respectively. The mechanism by which ThT dye indicates amyloid fibrils is that the ThT dye recognizes beta sheet structure of fibrils as fibrillation occurs, and its emission intensity steadily increases. Fibrillation lag time is a measure of time taken by insulin or an analogue thereof to begin to form fibrils. For the purposes of this disclosure, fibrillation lag time is determined by linear regression of the slope of the fitted curve of the emission spectra to time.

In some embodiments, the insulin analogue or a pharmaceutical composition thereof, as described herein, exhibits a fibrillation lag time (at 40° C. with rapid agitation) of more than about 5 hours, or more than about 10 hours, or more than about 15 hours, or more than about 20 hours, or more than about 25 hours, or more than about 30 hours, or more than about 35 hours, or more than about 40 hours, or more than about 45 hours, or more than about 50 hours, or more than about 55 hours, or more than about 60 hours, or more than about 65 hours, or more than about 70 hours, or more than about 75 hours, or more than about 80 hours, or more than about 85 hours, or more than about 90 hours, or more than about 95 hours, or more than about 100 hours, or more than about 125 hours, or more than about 150 hours, or more than about 200 hours, or more than about 250 hours.

In various embodiments, the insulin analogue or compositions described herein do not exhibit any decrease or a substantial decrease in fibrillation lag time upon formulation with polyphosphates (e.g., sodium triphosphate).

In some embodiments, the insulin analogue, as described herein, has lower mitogenic potential than commercially available insulin lispro.

The present invention in some aspects and embodiments, provides methods for determining pharmacokinetic parameters or pharmacokinetic profile of an API using, e.g., nonalogs. The invention further provides methods for determining a suitable or optimal API formulation using, e.g., nonalog compositions. The present invention further includes nonalog or compositions thereof that may be used for determining the pharmacokinetic parameters or pharmacokinetic profile of an API. The methods, as described herein, for determining PK properties of an API formulation minimizes stress and toxicity in the test subject, lowers cost, decreases the effects of inter-animal variability, and increases throughput. In one embodiment, the method allows for the study of multiple formulations in a single subject in a single experiment.

In some embodiments, the invention provides a method for determining pharmacokinetic (PK) parameters or profile of an API formulation. This method includes administering a plurality of inactive or non-potent analogue (nonalog) compositions of the API to a test subject and determining concentration of the nonalogs in one or more tissue samples from the test subject. The method also includes determining one or more pharmacokinetic parameters for the API formulation based on the concentration of the nonalogs in the test subject. In one embodiment, this method is used to determine PK parameters for a nonalog and use it as a proxy for determining the PK parameters for the corresponding API. Thus, this disclosure provides a method for making a pharmaceutical formulation of an API. This method includes administering to a test subject a plurality of nonalog compositions of the API and determining the concentrations of the nonalogs in one or more tissue samples from the test subject. The method also includes determining pharmacokinetic profiles for the nonalog compositions and formulating the API as pharmaceutical formulation having a desired pharmacokinetic profile. In one embodiment, the method further includes determining the desired pharmacokinetic profile based on the concentrations of the nonalogs in one or more tissue samples from the test subject. Once a desired pharmacokinetic profile or parameter for the nonalog composition is achieved, then, this API can be formulated in accordance with a selected nonalog composition, except, that the nonalog in the selected nonalog composition is replaced with the corresponding API. Other modifications to the API formulation may be made that do not substantially impact the pharmacokinetic profile. In another aspect, the invention provides a non-potent analogue (nonalog) or multiple nonalogs for a given API (e.g., insulin), which have substantially the same interactions with non-human test subjects, but are chemically or physically distinguishable.

This aspect includes compositions of the nonalogs, with different pharmaceutically acceptable carriers that impact pharmacokinetics in the test subject. These nonalog compositions are useful in determining pharmacokinetic parameters of various formulations of the corresponding API (e.g., insulin). In some embodiments, the invention provides a kit of at least three, at least four, at least five, or at least six nonalogs, which can be differentially formulated in accordance with this disclosure.

During drug discovery, candidate active pharmaceutical ingredients (APIs) (also called "drug substances") are designed and evaluated for a desired effect, which is generally to diagnose, cure, mitigate, treat, or prevent a particular disease or condition. For example, peptides might be evaluated for how well they bind to a cellular receptor to inhibit its action, or a small molecule might be evaluated for its antibiotic properties. When a particular API is chosen for further development, several methods or tools are typically used to optimize its activity. One of these methods or tools is a formulation of the API. An API's formulation comprises the chemical substances mixed with the API in order to confer optimized pharmacological properties. A formulated drug substance or API is called a drug product. The substances included in a formulation are called excipients. For example, a weak acid excipient might be included in an API formulation to make the API soluble in liquid. In another example, an ionic salt excipient might be combined with the API in order to mask charges in subcutaneous tissue to prevent charged surfaces on the API from being "trapped" by charged elements in the tissue and thereby enable the API to move more rapidly toward the bloodstream. Optimizing formulation plays a significant role in ensuring that the API has the time-action profile it is designed to have. Therefore, optimizing API formulation is an important step in drug development.

Pharmacokinetics (PK) is the study of the time course of absorption, distribution, metabolism, and elimination of a substance in an animal, e.g., a human or a non-human mammal. Absorption is the process of a substance (e.g., an API) moving from the administration site to the bloodstream. Distribution describes how a substance (e.g., an API) reaches different parts of a subject's body. Metabolism is the process of the substance being broken down or converted into metabolites upon administration to a subject. Elimination is the process of clearing the substance from the subject's body, often through the kidneys and into urine or through the bile and into feces. Examples of PK data (or parameters) include, but are not limited to, rate of absorption into the bloodstream, bioavailability, half-life, rate of metabolite generation, rate of clearance from the bloodstream, and rate of elimination from the test subject. A pharmacokinetic profile can include all these parameters or a sub-set of these parameters depending upon the objective of the PK study or need.

PK studies are useful for optimizing API formulations, and the importance of efficient and effective PK studies in animals is well recognized. PK data are essential in evaluating any drug product or API because studying how a drug enters, interacts with, and leaves a subject's body is important for determining dosage form, dosage concentration, and time between administration of doses. PK affects the pattern of appearance and disappearance of the API in the blood after the API formulation has been administered. This pattern is critical in creating the Pharmacodynamic (PD) or time-action profile of the drug as it drives the concentration of the API to which the target tissue is exposed over time.

However, during the drug product screening process, animal studies often present a bottleneck due to the cost and time needed to carry out the studies. Animal studies often have large inter-animal variation, and often the solution to minimize these variations is to use large numbers of animals to acquire relevant, and often redundant, data.

The cost of maintaining animal colonies and carrying out the resulting large number of studies, especially in large animals like pigs, can be cost-prohibitive. Nevertheless, studies in pigs can be particularly desirable, due to similarities in response to insulin with humans. Additionally, the space needed to maintain large colonies limits how many studies can be carried out simultaneously. Due to the large costs of carrying out formulation studies in animal models, often few formulations are evaluated during drug development, potentially foregoing formulations that are optimal and beneficial to patients. Animal studies, including PK studies, also aim to minimize stress to the animals being tested. For studies in large animal models, surgeries must often be performed to install catheters into the animals to allow repeated access to blood from the same site on the animal for the duration of a study. These catheters represent an infection risk and must be kept clean and accessible during the span of the study. Catheter installation and maintenance add cost and are extrinsic stressors for the animals used in the study. Even in smaller animals, repeated experiments carried out on the same animal can be a source of continuous, and often repeated, stress. A more efficient method of carrying out PK studies would therefore reduce stress in test animal colonies. The effects of the APIs being tested represent another cost and source of stress for the animals being tested. For example, pigs being treated with insulin analogs need to have their blood glucose levels monitored, and additional glucose must be given to these animals to avoid hypoglycemic events. APIs have other toxicities at high doses, limiting the frequency with which an individual animal can be studied.

Moreover, the economic and medical consequences of problems with drug absorption and variable bioavailability are immense. Failing to identify promising or potentially problematic drug candidates during the discovery and pre-clinical stages of drug development is one of the most significant consequences of problems with drug bioavailability. Accordingly, there is a need to develop a comprehensive, physiologically-based pharmacokinetic testing system capable of evaluating drug bioavailability and variability in humans. Furthermore, considering the urgent need to provide the medical community with new therapeutic alternatives and the current use of high throughput drug screening for selecting lead drug candidates, a comprehensive biopharmaceutical tool that can quickly provide pharmacokinetic parameters or profile is needed.

Thus, there remains a need for a method of optimizing API formulation that is more efficient, cost-effective, and minimizes stress and harm to the study animals.

In broad terms, the present invention in some aspects provides methods of evaluating the effects of formulations on PK parameters in animal studies whereby multiple nonalogs of an API with different formulations are administered to an animal substantially simultaneously. In one embodiment, blood is collected from the animal during the study at predetermined time points post-administration. The PK properties for each nonalog formulation are determined by evaluating the concentration of each nonalog in plasma samples over the course of the study. Because the nonalogs are all closely related and pharmacologically inactive, any change in PK parameters will be mostly or entirely due to the different formulations. This information can then be used to screen out formulations that do not meet the desired PK criteria or to refine formulations for improved PK parameters. The formulations with the desired characteristics can then be used for APIs.

In one embodiment, samples are extracted from the test subjects at pre-determined time points post-administration of the nonalog compositions. The samples (e.g., blood samples) contain all of the nonalogs used in the study. Number and frequency of time points for taking samples may be determined according to the desired resolution of PK data. Generally, more time points over the same time period will give greater resolution in the PK data obtained at the end of the study. Number and frequency of time points may also be determined according to the level of stress caused to the test subject for each sample taken. Using the concentrations of the different nonalogs from the samples taken over a time course, the effects of different formulations are evaluated by the chosen detection method. Once samples are taken from the study animals at predetermined time points post-administration, the concentration of each nonalog is determined in order to evaluate PK properties of the different formulations used in the study. Because each related nonalog has a different signature when using the chosen detection method, the concentrations of each nonalog over the course of the study can be evaluated from samples from a single study and used to determine the PK properties of each administered nonalog composition. After samples are evaluated for the concentrations of each nonalog over time, the data are evaluated. Formulations may or may not confer beneficial PK properties to their respective nonalogs, indicated by the concentrations of each nonalog in each sample over time, and formulations can either be chosen to proceed to more rigorous testing or eliminated from the screening process.

In some embodiments, the method comprises administering multiple nonalog compositions to a second subject and determining the concentrations of the nonalogs in one or more tissue samples from the second subject. A nonalog, that is administered to both the first subject and the second subject, is then selected and its clearance rate is determined in the second subject. Then, the absorption rate of the selected nonalog in the first subject is determined based on the clearance rate of the selected nonalog in the second subject. In this embodiment, clearance rate of a nonalog is calculated by administering nonalog(s) to one or more test subjects, e.g., two subjects, three subjects, or more. In one example of this embodiment, one or more nonalogs are administered to test subjects (e.g., a first subject and second subject). Then one or more tissue or other (e.g., blood) samples are obtained from the test subject(s) and concentrations of each nonalog (or a selected nonalog) is determined in each sample. The clearance rate of each (or selected) nonalog from the second test subject may then be determined in order to calculate the absorption rate of the formulation of that nonalog of the API administered to the first test subject. In one embodiment, the nonalog compositions are administered simultaneously or near simultaneously to the first subject and to the second subject. In another embodiment, the nonalog compositions are administered successively to the second subject. The second subject's sample can be taken, e.g., from blood, liver, kidney, lung, spleen, heart, brain. The tissue or other sample taken from the second subject can be the same as the first subject or a different tissue or source. In one embodiment, the subject (including the first subject or the second subject) may be administered multiple nonalogs, e.g., one to twenty-five nonalogs at the same time. In one embodiment, the subjects are administered two, three, four, five, six, seven, eight, nine, or ten nonalog compositions. An active drug substance or API suitable for use in the formulations and methods described herein is a therapeutically, prophylactically and/or diagnostically active drug substance (herein also abbreviated "active drug substance"). For example, in various embodiments, the API is a protein, a peptide, an antibody or a portion thereof, a small molecule, an oligonucleotide, or a polymer. In one embodiment, the API is insulin or a drug used to treat diabetes. Alternative APIs include analgesics, opioids, antipyretics, anesthetics, antimigraine agents, antiepileptics, anti-Parkinson agents, dopaminergic agents, antipsychotics, anxiolytics, sedatives, antidepressants, psychostimulants agents, dopamine, noradrenaline, nicotinic, alpha-adrenergic, serotonin, H3 antagonists used for ADHD and nootropics agents used in addictive disorders. In still further embodiments, the active substance is selected from therapeutic classes including centrally-acting analgesics, sedative-hypnotics, appetite suppressants, decongestants, antitussives, antihistamines, antiemetics, antidiarrheals, and drugs used to treat narcolepsy and attention deficit hyperactivity disorder. In certain embodiments, the active drug substance is associated with abuse syndromes and the active drug substance may, for example, be selected from opioids, CNS depressants, CNS stimulants, cannabinoids, nicotine-like compounds, glutamate antagonists, and N-methyl-D-aspartate (NMDA) antagonists.

Use of inactive or non-potent analogues allows administration of multiple nonalog compositions simultaneously or successively to a test subject. Simultaneous administration of fully active APIs at clinically relevant or effective concentrations would in most instances result in very high concentrations of the API in the test subject and likely cause toxicity. Even if administering high doses of a particular API did not cause toxicity, the effects of the active API on the animal would have to be dealt with, which would raise the cost of the study. Moreover, giving high doses of the API may affect the subject or its physiology in a way that the PK studies do not give reliable data. Likewise, administering low concentrations of fully active APIs in order to relegate toxicity could potentially alter the PK parameters of the API combined with its formulation, or result in blood concentrations of API that would be undetectable for analysis. Inactive or non-potent analogs allow for multiple, near-simultaneous or successive clinically relevant dosing of the test subject with reduced or eliminated risk for toxicity. This decrease in toxicity risk allows for reduced cost, efficiency, and subject welfare benefits.

Nonalogs could have a wide variety of designs. In one embodiment, the nonalogs are inactive, i.e., they possess no pharmacological/biological/chemical activity or only a portion of the pharmacological/biological/chemical activity of the API. In another embodiment, the nonalogs of an API differ from each other sufficiently so that multiple nonalogs can be detected in a single tissue sample (e.g., blood plasma sample). In yet another embodiment, the nonalog are sufficiently similar to the parent API such that no PK changes would be expected from the change or changes in the nonalog. In a preferred embodiment, the nonalogs possess no pharmacological/biological/chemical activity; differ from each other sufficiently so that multiple nonalogs can be detected in a single tissue sample; and are sufficiently similar to the parent API such that few or no PK changes would be expected from the change or changes in the nonalog.

In various embodiments, the nonalogs are produced in a recombinant DNA expression system or chemically synthesized. In one embodiment, nonalogs are isotopically labelled with different isotopes to increase specificity for their detection using a mass spectrometry detection method. In another embodiment, nonalogs are designed with different hydrophobicity to increase specificity using an HPLC detection method. In another embodiment, an amino acid with similar chemical properties but different mass is substituted in the peptide or protein sequence to increase specificity using ligand binding liquid chromatography tandem mass spectrometry (LBA-LC-MS/MS). This flexibility in molecular design provides a method to synthesize adequate amounts of material for statistically relevant population sizes.

The nonalog, in some embodiments, is an inactive or non-potent analogue of an API with about 75% or lower activity as compared to the fully active form of the API. In one embodiment, the nonalog has about 10% or lower activity as compared to the fully active form of the API. The activity of the API or the nonalog is, for example, biological, pharmacological, medicinal, or chemical activity. In some embodiments, the activity of the API or the nonalog is based on an in vitro or in vivo assay. The assay for measuring activity could be, e.g., enzyme linked immunosorbent assay, immunohistochemistry assay, flow cytometry, biochemical assays that measure binding affinity of the API/nonalog to its target (e.g., receptors) or measure inhibition of enzyme activity.

In one embodiment, the nonalog has similar physical, chemical, or biological structure as the API. For example, the nonalog has similar chemical structure, similar primary structure, similar secondary structure, similar tertiary structure, or similar quaternary structure to the API. In another embodiment, the nonalog has similar hydrophobic properties or similar surface charge pattern as the API. The term "hydrophobic properties" includes the overall hydrophobicity of the API or the nonalog and also hydrophobicity of portions of the API or the nonalog. For instance, the hydrophobic properties include hydrophobic nature of a protein has a whole or, e.g., a portion of the protein that is exposed on the surface of the protein or buried inside the protein's structure.

In various embodiments, the nonalog of a peptide or a protein (e.g., insulin) comprises an amino acid sequence having one or more amino acid mutations as compared to the API. In some embodiments, the one or more amino acid mutations may be independently selected from substitutions, insertions, deletions, and truncations. The nonalog could have, e.g., one mutation, two mutations, three mutations, four mutations, five mutations, six mutations, seven mutations, eight mutations, nine mutations, or ten mutations. In certain embodiments, the mutations include amino acid substitutions such as conservative amino acid substitutions, and/or non-conservative substitutions. In some embodiments, the nonalog is a protein or peptide having from 10 to 100 amino acids, where one or two amino acids are substituted, inserted, or deleted, leading to inactive or non-potent analogs. In some embodiments, the protein has more than 100 amino acids, and may have one or two additional substitutions, deletions, or insertions. In some embodiments, each nonalog in the set of nonalogs has a modification(s) at the identical positions relative to the API. In some embodiments, the nonalogs have an amino acid sequence that is within 90% identity to the amino acid sequence of the API, or within 95% identity to the amino acid sequence of the API, or within 98% or 99% identity to the amino acid sequence of the API. "Conservative substitutions" include those substitutions made within a group of amino acids with similar side chains, for example: the neutral and hydrophobic amino acids glycine (Gly or G), alanine (Ala or A), valine (Val or V), leucine (Leu or L), isoleucine (Ile or I), proline (Pro or P), tryptophan (Trp or W), phenylalanine (Phe or F) and methionine (Met or M); the neutral polar amino acids serine (Ser or S), threonine (Thr or T), tyrosine (Tyr or Y), cysteine (Cys or C), glutamine (Glu or Q), and asparagine (Asn or N); basic amino acids lysine (Lys or K), arginine (Arg or R) and histidine (His or H); and acidic amino acids aspartic acid (Asp or D) and glutamic acid (Glu or E). Further, standard amino acids may also be substituted by non-standard amino acids, for example, those belonging to the same chemical class. By way of non-limiting example, the basic side chain lysine may be replaced by basic amino acids of shorter side-chain length (Ornithine, Diaminobutyric acid, or Diaminopropionic acid). Lysine may also be replaced by the neutral aliphatic isostere Norleucine (Nle), which may in turn be substituted by analogues containing shorter aliphatic side chains (Aminobutyric acid or Aminopropionic acid). In some embodiments, the insulin nonalogs have from one to five mutations with respect to the sequence of Insulin Lispro, Insulin Aspart, or Fluorolog (Asp B10, ortho-monofluorophenylalanine-B24, lispro insulin). In some embodiments, these mutations are conservative mutations, with no more than one, two, or three non-conservative mutations or non-standard mutations.

In one embodiment, the mutations cause a reduction in activity of the nonalog, e.g., a reduction in the binding affinity or activity of the nonalog to the receptor or biological target of the API. In one embodiment, the nonalog may activate the corresponding API's receptor with reduced potency. In other embodiment, the mutations result in the nonalog to have reduced or ablated activating activity at the corresponding API's receptor or biological target.

In another embodiment, the nonalogs described here are modified to have reduced affinity or activity for one or more of its receptors or biological targets, which allows for attenuation of activity (inclusive of agonism or antagonism). In some embodiments, the mutations allow for the nonalog to have attenuated activity, such as, reduced binding affinity to a target, reduced enzymatic activity, reduced inhibition or activation of a target (e.g., a receptor) relative to unmutated, i.e., the API. In some embodiments, the activity of nonalogs can be determined by using in vitro and in vivo assays know to a person of skill in the art. The methods described herein relate to pharmacokinetic-based design of API formulation using administration of one or more nonalogs to a subject as a proxy for the API. In one embodiment, the nonalog compositions may be administered to the subject in order to determine which formulation to use for the corresponding API to obtain desirable absorption for the API, desirable liberation or release profile of the API from the composition, desirable distribution profile of the API in the subject, desirable metabolism profile of the API in the subject, or desirable excretion profile of the API in the subject. In some embodiments, the methods disclosed herein measure absorption effects of one or more formulations. As metabolism of an API produces predictable metabolites, the concentration of metabolites of one or more nonalogs over time could be determined via LC-MS/MS, or another detection method, to calculate metabolic rate. The methods described herein also facilitate prediction of the fate of an API in a mammal based on absorption of the nonalog and one or more additional bioavailability parameters including distribution, metabolism, elimination, and optionally toxicity.

In this aspect, the method allows for optimization of an API formulation using nonalog composition as a proxy. The nonalog compositions can have several iterations of excipients (or their concentrations) are administered to the subject and a nonalog composition is selected based on certain desirable characteristics. Then, this selected nonalog composition is used to design/optimize the corresponding API's formulation.

In some embodiments, elimination rate is calculated by detecting the presence of one or more nonalogs and its/their metabolite(s) in the urine or feces of a test subject.

In some embodiments, one or more PK parameters can be measured to prepare a PK profile. This PK profile, generated using nonalog compositions and methods of the invention, can be uni- or multi-dimensional output that reflects one or more PK parameters of the subject with respect to the API. The results can be used to profile or rank the nonalog compositions by a selected PK parameter, and optionally, absorption and one or more additional bioavailability parameters and toxicity.

In some embodiments, the nonalog composition mimics a desired API formulation or an existing API formulation. In some embodiments, the API formulation is such that it mimics the nonalog formulation. The term "mimic" as used herein in the context of a formulation or a composition means that two or more compositions have similar ingredients. For example, an API formulation that mimics a nonalog composition would have similar ingredients in similar concentrations as the nonalog composition, except that the nonalog in the composition is replaced by the API. Similarly, a nonalog composition that mimics an API formulation would have similar ingredients in similar concentrations as the API formulation, except that the API in the formulation is replaced with the nonalog.

In some embodiments, the reason for a nonalog composition to mimic an API formulation is to use the nonalog formulation as a control or to test an existing API formulation in order to assess any variations in PK parameters in a multiplex testing environment where multiple nonalog compositions are administered to the subject. In one embodiment, a known API formulation is administered along with the nonalog compositions, e.g., to use as a control or to correct for errors that might be introduced during the study or to compare known PK parameters for the API formulation with the PK parameters obtained after administration of the API formulation in combination with nonalog compositions.

In another embodiment, several nonalog having different compositions are administered to a subject and, based on desired PK characteristics or responses in the subject, a nonalog composition is selected. The API formulation is then formulated to mimic the selected nonalog composition.

The nonalog compositions disclosed herein may be administered to the subject simultaneously, near simultaneously, or successively. For example, in one embodiment, a plurality of nonalog compositions are administered to the subject simultaneously, i.e., together with other nonalogs. In one embodiment, the nonalogs are administered via the same route of administration to the subject or via different routes of administration. For example, one nonalog could be administered orally and another one could be administered intravenously. It should be noted that simultaneous administration, in the context of this embodiment, could mean that all nonalogs are administered together or within a short time span of each other (near simultaneously). For example, in a near simultaneous administration, all the nonalogs are administered within a time span ranging from about 1 minute to about 30 minutes.

Simultaneous or near-simultaneous administration of the nonalogs or their respective compositions in a single test subject allows increased efficiency and decreases the cost for PK formulation studies. This is because fewer test subjects are needed. Another benefit is that it allows simultaneous detection of multiple nonalogs in a single tissue sample. This increases throughput for evaluating PK parameters of different formulations, and reduces time and cost required to carry out these studies. Another benefit of this method is the reduced stress levels in the test subjects. Yet another benefit of this method is a decrease in inter-animal variation, as multiple formulations can be evaluated in one study on the same test subject.

In some embodiments, the nonalogs or their respective compositions are administered successively to a test subject. Successive administration minimizes the number of animals needed to conduct a PK study and allows for conducting PK studies without overloading the subject with several nonalogs in a given time span. Successive administration could be conducted in such a manner such that a second batch of nonalogs is administered after the elimination of a first batch of nonalogs from the subject. Successive administration could also be conducted to study absorption rates of nonalogs such that a second batch of nonalogs is administered after the complete absorption of the second batch of nonalogs. A second or successive batch of nonalogs could be administered, for example, from about 35 minutes to about 24 hours after administration of a first batch of nonalogs or compositions thereof. Note that these time spans are exemplary and the time span between successive administrations of nonalogs or compositions of nonalogs could be calculated based on, e.g., the elimination rates of nonalogs, in vivo half-life of the nonalogs, or the absorption rates of the nonalog compositions. For instance, in one embodiment, where the nonalogs or compositions thereof are fast-acting or rapidly-absorbing, a second administration can be made shortly after (e.g., within about 35 minutes) of the first administration so that the second administration avoids the plasma concentration maxima of the first fast-acting nonalog composition in the subject, thereby, reducing any potential adverse effects due to high concentration of the nonalogs in the subject.

In various embodiments, the tissue samples are collected at multiple time intervals before or after administration of the nonalog compositions to the test subject.

Routes of administration of nonalogs and their formulations into the test subject may vary. When the sample taken from the subject is blood, then the drug must eventually be present in the bloodstream so that blood samples can be taken from the animal to determine concentrations of the nonalog(s) over time to evaluate PK differences conferred by the different formulations being tested. It is envisioned that routes of administration could vary not only between studies, but between nonalogs in the same study in the same test subject. In some embodiments, nonalog compositions are administered to the subject using one or more of the following routes: enteral (e.g., buccal or sublingual, oral (PO), rectal (PR)), parenteral (e.g., intravascular, intravenous bolus, intravenous infusion, intramuscular, subcutaneous injection), inhalation or via a nasal route, transdermal (percutaneous), intradermally, intraperitoneally, or intrathecally. In one embodiment, the selected route of administration determines the type and/or source of assay employed for obtaining PK parameters. For instance, for oral administration can be used to determine the rate of liberation or dissolution of a nonalog composition in a tablet or capsule. In another embodiment, multiple routes of administration are used to determine distribution of the nonalog to a particular tissue. For example, oral, hepatic, systemic and blood brain barrier assays may be used to obtain distribution parameters for compounds that target brain tissue. In some embodiments, the pharmacokinetic parameters are determined using the concentration of the nonalogs in one or more tissue or other samples, e.g., without limitations, blood, bone, liver, kidney, lung, spleen, heart, brain, gastrointestinal tract, spine, spinal fluid, cerebrospinal fluid, eye, mouth, or muscle. In a preferred embodiment, the tissue sample is a blood sample.

In some embodiments, tissue samples collected from subjects, before or after the administration of nonalog compositions, are used to determine the concentration of the nonalog, API, or metabolites of the nonalog. In one embodiment, the concentration of the nonalog, API, or metabolites thereof are measured using a single assay or analytical method. For example, in one instance, several tissue samples are collected from a subject and are evaluated in single assay such as LC-MS in one step. In another embodiment, several tissue samples are analyzed using multiple assays or analytical methods. For example, one set of tissue samples may be analyzed using liquid chromatography and ultraviolet detection and another set of samples from the same subject may be analyzed using LC-MS. The choice of analytical method will depend on the nonalogs to be analyzed and can be determined based on the physical or chemical characteristics of the nonalog or API. The analytical methods that may be used for the methods described herein, include without limitation, LC-MS/MS, LC-MS, immunoassay, radioimmunoassay, or chromatography. There are various methods for detecting concentrations in blood of an API over time to determine PK properties. Immunoassays, which use specific antibodies that bind to the API in a quantitative manner, can be useful but an appropriate antibody must be available. Chromatography, in which the test solution is separated in either a gas or liquid phase by partitioning with a solid or liquid phase, can also be useful for quantitation of an API. Liquid chromatography paired with mass spectroscopy (LC-MS) or tandem mass spectroscopy (LC-MS/MS) are very useful methods for accurately quantitating concentrations of APIs in solutions. Ligand binding assays can be coupled with LC-MS/MS to extract API from biological matrices to enhance quantification in urine, serum, plasma or tissue samples.

In some embodiments, an immunoassay is performed to determine nonalog concentration in a tissue sample. In another embodiment, U/HPLC is performed to determine nonalog concentration in a tissue sample. In another embodiment, LC-MS/MS is performed to determine nonalog concentration in a tissue sample. In another embodiment, LBA-LC-MS/MS is used to quantify nonalogs in a biological matrix. This method allows precise calculation of peptide concentrations in a solution, even when the solution contains many components. This is especially beneficial for the present invention, in which the formulations being evaluated could potentially be very complex and contain multiple components.

In some embodiments, the nonalogs described herein are labeled so that they can be easily detected in an analytical method. In some embodiments, labeling does not affect the pharmacokinetic, physical, chemical or pharmacological behavior of the nonalog. In other embodiments, the labeling causes the nonalog to lose its activity as compared to the API. The nonalogs described herein could be labeled with a radio label, a fluorescent label, a heavy isotope of, e.g., carbon, oxygen, hydrogen, sulfur, or nitrogen.

The nonalogs, APIs and methods described herein are useful for evaluating PK parameters in a wide range of formulations or compositions. The compositions or formulations may include different concentrations of the API. The concentration may be, for example, a high, medium, or low concentration. In this instance, the methods of this invention may be used to evaluate the impact of API concentration and drug product volume on the pharmacokinetic characteristics of the formulation. The compositions or formulations may also include a wide range of excipients.

In various aspects and embodiments, the pharmaceutical compositions of insulin analogues described herein comprise one or more pharmaceutically acceptable excipients or carriers suitable for subcutaneous or intra-dermal administration. A particular excipient may have two or more functions in a formulation. Table 1 below provides a list of exemplary excipients and their exemplary functions in a formulation.

In certain embodiments, the pharmaceutical composition may include one or more buffering agents for maintaining a formulation at a specific pH. Exemplary buffering agents include, but are not limited to, sodium phosphate, arginine, TRIS (2-amino-2-hydroxymethyl-1,3-propanediol), glycylglycine, L-Histidine, HEPES, bicine, sodium acetate, sodium carbonate, sodium citrate, sodium dihydrogen phosphate, disodium hydrogen phosphate, bicine, tricine, malic acid, succinate, fumaric acid, tartaric acid, aspartic acid, ethylendiamine or mixtures thereof. See, for example, U.S. Pat. No. 6,906,028 and U.S. Patent Publication No. 2012/0225810, the entire contents of which are hereby incorporated by reference. In some embodiments, the pharmaceutical compositions of the present invention include from about 5 mM to about 100 mM Tris. In various embodiments,

TABLE 1

Potential Excipients

| | Isotonicity | Preservative | Buffer | Stabilizing | Solubilizing | Anti-aggregation | Trans-membrane | Absorption |
|---|---|---|---|---|---|---|---|---|
| Glycerol | ✓ | | | ✓ | | | | |
| Mannitol | ✓ | | | ✓ | | | | |
| Sorbitol | ✓ | | | ✓ | | | | |
| Propylene glycol | ✓ | | | | | ✓ | | |
| Phenol/m-cresol | | ✓ | | ✓ | | | | |
| TRIS | | | ✓ | ✓ | | | | |
| Arginine | | | ✓ | ✓ | ✓ | ✓ | | |
| Histidine | | | ✓ | ✓ | | ✓ | | |
| Aspartic acid | | | ✓ | | ✓ | | ✓ | |
| Glutamic acid | | | | ✓ | ✓ | | ✓ | |
| Proline | | | | | | ✓ | | |
| Lysine | | | | | | ✓ | | |
| Magnesium | | | | | ✓ | | | ✓ |
| Citrate | | | ✓ | | ✓ | ✓ | ✓ | |
| Nicotinamide | | | | ✓ | | ✓ | | |
| Surfactants | | | | ✓ | | ✓ | | ✓ |
| Alkylglycosides | | | | ✓ | | ✓ | | |
| Ethylenediamine-tetraacetic Acid (EDTA) | | | | | | | | ✓ |
| Iloprost | | | | ✓ | | | | ✓ |

In various embodiments, the pharmaceutical composition includes one or more of a pharmaceutically acceptable buffer, stabilizing agent, surfactant, solubilizing agent, anti-aggregation agent, diffusion-enhancing agent, absorption enhancing agent, and preservative. These agents can be used in combination and function synergistically to, for example, enhance insulin absorption, promote a more rapid insulin pharmacokinetics, and/or increase insulin stability.

In certain embodiments, the pharmaceutical composition may include one or more agents that maintain or adjust the tonicity of the formulation. Such agents include, but are not limited to, glycerol, mannitol, sorbitol, lactose, dextrose, trehalose, sodium chloride, and propylene glycol (see, for example, U.S. Patent Publication No. 2012/0225810, the entire contents of which are hereby incorporated by reference). In various embodiments, the formulation may be hypertonic or hypotonic. For example, the pharmaceutical composition may contain one or more agents designed to make the formulation hypertonic. Exemplary agents include any agents that are soluble in the formulation and cannot freely permeate the plasma membrane of cells, such as glycerin, dextrose, mannitol, NaCl, and KCl. In some embodiments, the pharmaceutical composition comprises about 1 mg/ml to about 100 mg/mL glycerin. In various embodiments, the pharmaceutical composition includes about 1 mg/mL to about 50 mg/mL, or about 8 mg/mL to about 25 mg/mL of glycerin (e.g., about 16 mg/ml).

the pharmaceutical compositions of the present invention include about 5 mM, about 10 mM, about 20 mM, about 30 mM, about 40 mM, about 50 mM, about 60 mM, about 70 mM, about 80 mM, about 90 mM, or about 100 mM Tris. In one embodiment, the pharmaceutical composition includes about 50 mM Tris.

In certain embodiments, the pharmaceutical composition may include one or more stabilizing agents for stabilizing the insulin formulations. Exemplary stabilizing agents include, but are not limited to, zinc (e.g., at a molar ratio less than 0.05 to the insulin in the formulation), phenol, m-cresol, benzoate salts, TRIS, non-reducing carbohydrates (e.g., mannitol or dextran), surfactants (e.g., polysorbates such as TWEEN, bile salts, salts of fatty acids, or phospholipids, partial and fatty acid esters and ethers of polyhydric alcohols, of glycerol or sorbitol and of sucrose, and polyols, partial and fatty acid esters and ethers of polyhydric alcohols such as SPAN polysorbate, MYRJ, BRIJ, TRITON, and CREMOPHOR, poloxyethylene ether, and apolyethylene glycol ether), amino acids (e.g., L-Arginine, L-Glutamic acid, L-histidine, or L-methionine), alkylsaccharides (e.g., dodecyl-β-D-maltoside, tridecyl maltoside, tetradecyl maltoside, sucrose mono-dodecanoate, sucrose mono-tridecanoate, sucrose mono-tetradecanoate), A-L-S-L-A compounds, chromium salts, acetone, methyl ethyl ketone, propyl methyl ketone, isopropyl methyl ketone, pyruvic acid, glyoxylic acid, alpha-ketobutyric acid, alpha-ketoglutaric acid, acetoacetic acid, pyridoxal, pyridoxal pyrophosphate, and iloprost singly or in combination.

In certain embodiments, the pharmaceutical composition may include one or more solubilizing agents to avoid precipitation of the insulin or insulin analogue within a formulation and to enhance solubility of the insulin or insulin analogue. Exemplary solubilizing agents include, but are not limited to, L-Arginine, L-arginine analogues or di- and tri-peptides containing arginine, guanidine, magnesium, alcohols, alcohol esters of organic acids, nitrogen-containing solvents, phospholipids, acetic acid, ascorbic acid, citric acid, glutamic acid, aspartic acid, succinic acid, fumaric acid, maleic acid, adipic acid, agmatine, 4-guanidinobenzoic acid, guanidoacetic acid, guanidinosuccinic acid, and co-polyamino acids, singly or in combination.

In certain embodiments, the pharmaceutical composition may include one or more anti-aggregation agents to avoid insulin aggregation in solution. Exemplary anti-aggregation agents include, but are not limited to, arginine, polysorbate 20, histidine, proline or proline derivatives, sulfobutyl ether-β-cyclodextrin, the tripeptide HTD, argininium ion or lysine, and propylene glycol, citric acid, and nicotinamide.

In certain embodiments, the pharmaceutical composition may include one or more transmembrane agents for facilitating the permeation and diffusion of insulin or an insulin analogue through membranes. Exemplary transmembrane agents include, but are not limited to, antennapedia protein, HSV Type 1 protein VP22, and HIV Tat protein, singly or in combination.

In certain embodiments, the pharmaceutical composition may include one or more absorption enhancing agents for facilitating the absorption of insulin or insulin analogue by any of a variety of mechanisms. Exemplary absorption enhancing agents include, but are not limited to, surfactants (e.g., bile salts, salts of fatty acids, or phospholipids), nicotinic agents (e.g., nicotinamide, nicotinic acid, niacin, niacinamide, vitamin B3 and any salts thereof), pancreatic trypsin inhibitor, magnesium salts, poly-unsaturated fatty acids, didecanoyl phosphatidylcholine, aminopolycarboxylate, tolmetin, sodium caprate, salicylic acid, oleic acid, linoleic acid, EPA, DHA, benzylic acid, NO donors (such as 3-(2-hydroxy-1-(1-methylethyl)-2-nitrosohydrazino)-1-propanamine, N-ethyl-2-(1-ethyl-hydroxy-2-1-nitrosohydrazino)-ethanamine, or S-nitroso-N-acetylpenicillamine), a bile acid, a glycine-conjugated form of a bile acid, sodium ascorbate, potassium ascorbate, sodium salicylate, potassium 5 salicylate, acetyl-salicylic acid, salicylosalicylic acid, aluminum acetylsalicylate, choline salicylate, salicylamide, lysine acetylsalicylate, exalamide, diflunisal, EDTA, acetic acid, ascorbic acid, citric acid, glutamic acid, aspartic acid, succinic acid, fumaric acid, maleic acid, adipic acid, polyphosphates, and ethenzamide, singly or in combination.

In certain embodiments, agents that minimize active agent (e.g., insulin) degradation may be included in the pharmaceutical composition. Without wishing to be bound by theory, it is believed that such agents inhibit the activities of neutrophils, monocytes, macrophages, lymphocytes, and platelets which accumulate within the granulation tissue following tissue trauma and release proteases, lipases, oxygen radicals, IL-1, IL-6, IL-8, MCP-1, and TNF that degrade insulin surrounding the infusion catheter. These agents include, but are not limited to, glucocorticoids such as dexamethasone, cortisol, solumedrol, and medrol, anesthetic such as lidocaine, bupivacaine, procaine, etidocaine, ropivacaine, mepivacaine, isoflurane, halothane, sevoflurane, desflurane, and enflurane, aprotinin or trasylol, aspirin and non-steroidal anti-inflammatory drugs (NSAIDs), cromolyn sodium, and immunosuppressant drugs such as cyclosporin, tacrolimus, and sirolimus, singly or in combination.

In certain embodiments, the pharmaceutical composition may include one or more diffusion enhancing agents such as base-substance diffusion enhancing agents. Exemplary diffusion enhancing agents include, but are not limited to, glycosaminoglycanases (e.g., hyaluronidase).

In certain embodiments, the pharmaceutical composition may include one or more preservatives for preventing growth of microorganisms. Exemplary preservatives include, but are not limited to, phenol, meta-cresol, methylparaben, propylparaben and sodium benzoate. In various embodiments, the pharmaceutical composition includes about 0.1 mg/mL to about 10 mg/mL m-cresol. In embodiments, the pharmaceutical composition includes about 0.1 mg/mL, about 0.5 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, or about 10 mg/mL of m-cresol. In one embodiment, the pharmaceutical composition includes about 3.2 mg/mL of m-cresol.

In various embodiments, the pharmaceutical composition may include one or more vasodilation agents, anti-inflammatory agents, anti-thrombotic agents, anti-degradation agents, insulin-binding antagonist, anti-fibrotic agents, antioxidants, anti-proliferatives, nerve-calming agents, and antibiotics. See, e.g., U.S. Pat. No. 9,901,622, the entire contents of which are hereby incorporated by reference in their entirety. These agents can be used in combination with any other excipients and agents described herein and may function synergistically to, for example, enhance insulin absorption, promote a more rapid insulin pharmacokinetics, and increase stability of insulin or insulin analogue. In some embodiments, the composition comprises a prostacyclin PGI$_2$ analogue, such as iloprost or treprostinil.

In some embodiments, iloprost is present in the pharmaceutical composition at a concentration of about 1 μg to about 100 ug/mL, or optionally at a concentration of about 5 μg/mL to about 50 μg/mL, or optionally at a concentration of about 10 μg/mL to about 25 μg/mL.

In some embodiments, the pharmaceutical composition comprises one or more polyphosphate compounds. In various embodiments, the polyphosphate is selected from one or more of a pyrophosphate, a triphosphate, a trimetaphosphate, and tetraphosphate. The polyphosphate may be used in their acidic form or in various salt forms, e.g., as alkali (e.g., sodium or potassium) salts or alkaline metal (e.g., calcium and magnesium) salts. In some embodiments, the polyphosphate comprises sodium triphosphate. In these embodiments, the concentration of polyphosphates (e.g., sodium triphosphate) in the composition is from about 1 mM to about 100 mM, or from about 1 mM to about 50 mM, or from about 1 mM to about 40 mM, or from about 5 mM to about 50 M. In some embodiments, the concentration of polyphosphate in the composition is about 5 mM, about 10 mM, about 15 mM, about 20 mM, about 25 mM, about 30 mM, about 35 mM, about 40 mM, about 45 mM or about 50 mM. In some embodiments, the concentration of polyphosphate in the composition is from about 10 mM to about 100 mM, or from about 10 mM to about 50 mM. In some embodiments, the concentration of the polyphosphate in the composition is from about 15 mM to about 35 mM. In some embodiments, the concentration of the polyphosphate is from about 10 mM to about 30 mM. In some embodiments, the concentration of the polyphosphate is about 20 mM, where the polyphosphate is optionally sodium triphosphate.

In certain embodiments, agents that increase active agent (e.g., insulin) diffusion, increase lymph flow by increasing muscle movement and minute ventilation, increase the flow of active agent (e.g., insulin) into the lymphatic vessels, increase absorption through capillary and venule walls into plasma, and/or increase blood flow through adipose tissue capillaries and venules may be included in the pharmaceutical composition (see, e.g., U.S. Pat. No. 9,901,622, the entire contents of which are hereby incorporated by reference in their entirety).

In various embodiments, the pharmaceutical composition of the present invention provides an onset of insulin activity (e.g., time of first positive glucose infusion rate in a euglycemic clamp, or $T_{onset}$) of less than about 40 minutes after administration, or less than about 30 minutes, or less than about 20 minutes, or less than about 15 minutes, or less than about 10 minutes, or less than about 5 minutes after administration in various embodiments. In various embodiments, the pharmaceutical composition provides a rapid insulin absorption profile as measured by, for example, $C_{max}$ and/or $T_{max}$. As used herein, $C_{max}$ is the maximum or peak concentration of a drug observed after its administration. As used herein, $T_{max}$ is the time at which maximum concentration ($C_{max}$) occurs. In certain embodiments, the pharmaceutical composition reaches a ½ $T_{max}$ Early at less than about 120 minutes, or less than about 90 minutes, or less than about 60 minutes, or less than about 50 minutes, or less than about 40 minutes, or less than about 30 minutes, or less than about 20 minutes, or less than about 15 minutes after administration.

In various embodiments, the pharmaceutical composition provides a short duration of insulin activity. In certain embodiments, the pharmaceutical composition provides a duration of insulin activity of about 6 hours or less, about 5 hours or less, about 4 hours or less, about 3 hours or less, or about 2 hours or less after administration. In some embodiments, duration of activity is measured as the time to which insulin action subsides to less than ½ maximal activity.

In various embodiments, the pharmaceutical composition provides enhanced storage stability. In certain embodiments, the pharmaceutical composition is stable for at least about 1 month, or at least about 3 months, or at least about 6 months, or at least about 12 months, or at least about 18 months, or longer, at 25° C. without substantial formation of insulin fibrils.

In further embodiments, the pharmaceutical composition maintains at least about 60% potency, about 70% potency, about 80% potency, about 90% potency, or about 95% potency after six months at 25° C. In another embodiment, the pharmaceutical composition maintains at least about 60% potency, about 70% potency, about 80% potency, about 90% potency, or about 95% potency after 9 months at 30° C. In a further embodiment, the pharmaceutical composition maintains at least about 60% potency, about 70% potency, about 80% potency, about 90% potency, or about 95% potency after 12 months at 25° C.

In some embodiments, the pharmaceutical composition is formulated for subcutaneous administration, and may be formulated as an aqueous formulation. In some embodiments, the formulation is provided in infusion devices, prefilled insulin pumps or prefilled injection pens and/or single or multiple dose vials or cartridges for subcutaneous administration. For example, the formulation may be provided in vials containing from 1 to about 1000 bolus doses, or from 1 to about 100 bolus doses, or from 1 to about 50 bolus doses, or from 1 to about 25 bolus doses. In some embodiments, the vial or cartridge is sufficient for providing a daily, weekly, or monthly insulin requirement for a patient. Vials or cartridges may contain the doses, for example, in about 3 mL to about 50 mL of total volume, such as from about 3 mL to about 10 mL of total volume. A bolus dose will generally have an injectable volume of 1 mL or less, such as about 0.5 mL or less, or about 0.2 mL or less, or about 0.1 mL. For example, the formulation can be provided in a prefilled reservoir inside a disposable insulin pump that contains about 0.5 mL of volume, about 1.0 mL of volume, about 1.2 mL of volume, about 1.5 mL of volume, about 2 mL of volume, or about 2.5 mL of volume. It will be appreciated that the actual dose of insulin or insulin analogue to be administered according to the present invention will vary according to, for example, the particular dosage form and the mode of administration, as well as each patient's disease and weight.

The pH of insulin compositions of the present invention is typically 7.0 to 7.8 and it is adjusted using physiologically appropriate acids and bases, typically hydrochloric acid 10% and sodium hydroxide 10%. In some embodiments, the pH is in the range of about 7.2 to about 7.6, with 7.4±0.1 as a common target pH.

Individual doses of the insulin or insulin analogue described herein can be formulated at, for example, about 1U/mL (1 insulin unit per mL) to about 2000 U/mL, or about 1 U/mL to about 1000 U/mL, or about 1 U/mL to about 500 U/mL, or about 1 U/mL to about 400 U/mL, or about 1 U/mL to about 300 U/mL, or about 1 U/mL to about 200 U/mL, or about 1 U/mL to about 100 U/mL, or about 1 U/mL to about 50 U/mL, or about 1 U/mL to about 10 U/mL. In some embodiments, the formulation contains from about 100 U/mL to about 1000 U/mL, or from about 100 U/mL to about 500 U/mL.

In various embodiments, the pharmaceutical composition does not include added zinc, or contains less than 0.05 moles of zinc per mole of insulin. In various embodiments, the pharmaceutical composition does not include magnesium.

In some embodiments, the pharmaceutical compositions comprises one or more anti-inflammatory agents and/or one or more anti-fibrotic agents. In various embodiments, the pharmaceutical composition comprises or consists of or consists essentially of a pharmaceutically acceptable buffer, a solubilizing agent, a vasodilator, an absorption enhancer, a tonicity agent, a preservative, and a stabilizing agent.

For example, an exemplary rapid acting formulation for the analogue designated T-1123 comprises 5 to 100 mM citrate, 1 to 10 mM EDTA, 0.25 to 30 µg/mL iloprost, 0.5 to 10 mM Mg', 1 to 50 mM Tris (pH 7.4), and 1 to 25 mg/ml glycerin. For example, an exemplary rapid acting formulation for the analogue designated T-1123 comprises about 45 mM Citrate, about 6.2 mM EDTA, about 15 µg/mL iloprost, about 4 mM Mg', about 10 mM Tris (pH 7.4), and about 16 mg/mL glycerin. For example, another exemplary rapid acting formulation for the analogue designated T-1123 comprises about 50 mM Tris buffer (pH 7.4), about 3.2 mg/mL m-Cresol, about 16 mg/mL glycerin, and about 20 mM sodium triphosphate.

In some aspects, the invention provides methods of treating or preventing a condition in a patient, by administering an insulin analogue or pharmaceutical composition described herein. In some embodiments, the present invention provides methods for treating a subject with diabetes or other condition treated with insulin or an analogue thereof, using any of the pharmaceutical compositions or formulations including insulin or insulin analogues as described herein. In an embodiment, the subject has type 1 diabetes or type 2 diabetes. In some embodiments, the patient exhibits insulin resistance. In a further embodiment, the subject has gestational diabetes or prediabetes.

Optionally, the subject may suffer from a metabolic disease for which insulin administration can be beneficial, such as obesity or metabolic syndrome. As used herein, the term "metabolic disease" refers to a group of identified disorders in which errors of metabolism, imbalances in metabolism, or sub-optimal metabolic homeostasis occur.

In an embodiment, the metabolic disease is obesity. For example, the subject may suffer from central obesity. In some embodiments, the obesity is one of simple obesity (alimentary obesity; usually resulting from consumption of more calories than the body can utilize), secondary obesity (usually resulting from an underlying medical condition, such as, for example, Cushing's syndrome and polycystic ovary syndrome), and childhood obesity. In some embodiments, the obesity is classified as: Class I, which includes a BMI between 30 and 34.99; Class II, which includes BMIs of 35 to 39.99; and Class III, which includes a BMI of over 40. Further, the present invention provides for obesity of any of classes I, II, or III that is further classified as severe, morbid, and super obesity.

In another embodiment, the metabolic disease is lipoatrophic diabetes. For example, the subject may have no fat anywhere or in certain body areas and may require very large doses of exogenous insulin to maintain euglycemia. In another embodiment, the metabolic disease is gestational diabetes, latent autoimmune diabetes in adults (LADA), and maturity onset diabetes of the young (MODY).

In a further embodiment, the present invention provides methods of treating a subject who is prediabetic using any of the analogues and pharmaceutical compositions described herein.

Prediabetes, also referred as impaired fasting glucose (IFG) or impaired glucose tolerance (IGT), is a precursor condition to type 2 diabetes. Prediabetes is diagnosed when fasting plasma glucose is between 100 to 125 mg/dL (5.56-6.94 mmol/L); or plasma glucose level is between 140 to 199 mg/dL (7.78-11.06 mmol/L) at 2-hours post-glucose load of 75 g; or an HbA1c level between 5.7 and 6.4%. Without intervention and appropriate treatment, people with prediabetes are at risk for developing type 2 diabetes.

The pharmaceutical composition and/or the formulation may be used to administer insulin before or during a meal. Due to the rapid absorption, the delivered insulin can shut off the conversion of glycogen to glucose in the liver, thereby preventing hyperglycemia. In an embodiment, the pharmaceutical composition and/or formulation are used to administer rapid action insulin at less than about 30 minutes, less than about 20 minutes, less than about 15 minutes, less than about 10 minutes, or less than about 5 minutes before a meal, or about the time of commencing a meal. In an embodiment, the pharmaceutical composition and/or formulation are used for administering insulin within about 10 minutes to about 20 minutes of commencing a meal (e.g., before or after commencing a meal). In certain embodiments, the subject is undergoing a regimen of basal insulin formulation or a basal insulin analogue formulation. The basal insulin may be administered from one to three times daily as a bolus injection.

In various embodiments, the pharmaceutical composition or formulation is administered at least one time, at least two times, at least three times, at least four times, at least five times or more daily in connection with or independent of meals. In an embodiment, the pharmaceutical composition or formulation is administered at least three times daily in connection with meal consumption. In certain embodiments, the pharmaceutical composition or formulation is administered (or delivery is activated) upon hyperglycemia. In an embodiment, the pharmaceutical composition is administered in an insulin pump, such as a tubed pump or a patch pump. In an embodiment, the insulin pump administers the pharmaceutical composition according to direct human input or according to an algorithm that calculates doses based on input from one or more sensors such as glucose or activity or other sensors. In an embodiment, the pharmaceutical composition is delivered in both basal and bolus doses of variable sizes.

In certain embodiments, the pharmaceutical composition or formulation is administered as a bolus subcutaneous injection. For example, administration may be achieved through a single bolus subcutaneous injection. In some embodiments, the pharmaceutical composition and/or formulation is automatically administered upon a detection of low or declining blood glucose levels. In some embodiments, the pharmaceutical composition is administered as a single-bolus subcutaneous injection or infusion.

In some embodiments, the volume of the pharmaceutical composition or formulation administered varies. In some embodiments, the volume of the composition delivered varies. In various embodiments, the injectate volume is less than about 3 ml, less than about 2.9 ml, less than about 2.8 ml, less than about 2.7 ml, less than about 2.6 ml, less than about 2.5 ml, less than about 2.4 ml, less than about 2.3 ml, less than about 2.2 ml, less than about 2.1 ml, less than about 2 ml, less than about 1.9 ml, less than about 1.8 ml, less than about 1.7 ml, less than about 1.6 ml, less than about 1.5 ml, less than about 1.4 ml, less than about 1.3 ml, less than about 1.2 ml, less than about 1.1 ml, less than about 1.0 ml, less than about 0.9 ml, less than about 0.8 ml, less than about 0.7 ml, less than about 0.6 ml, less than about 0.5 ml, less than about 0.4 ml, less than about 0.3 ml, less than about 0.2 ml, or less than about 0.1 ml, or less than about 90 µl, or less than about 80 µl, or less than about 70 µl, or less than about 60 µl, or less than about 50 µl, or less than about 40 µl, or less than 30 µl, or less than about 20 µl, or less than about 10 µl, or less than about 9 µl, or less than about 8 µl, or less than about 7 µl, or less than about 6 µl, or less than about 5 µl, or less than about 4 µl, or less than about 3 µl, or less than about 2 µl, or less than about 1 µl, or less than about 0.5 µl, or less than about 0.1 µl, inclusive of all values and ranges therebetween.

The present invention is further illustrated by the following non-limiting examples.

EXAMPLES

Example 1: Discovery of a Two-Chain Insulin with Optimized Stability

US 2019/0322719, which is hereby incorporated by reference, describes rapid acting insulin analogs with particular mutations in about 16 sites that could potentially be mutated to favorable effect (see Table 1 therein). Taken together, all of these potential mutations define an enormous space of potential analogs (See Table 2).

US 12,622,949 B2

29

TABLE 2

Potential Favorable Substitutions

| Position | # of Potentially Favorable Substitutions |
|----------|------------------------------------------|
| A8 | 18 |
| A12 | 10 |
| A13 | 8 |
| A14 | 8 |
| A17 | 10 |
| A21 | 7 |
| B1 | 2 |
| B2 | 4 |
| B3 | 4 |
| B13 | 11 |
| B17 | 9 |
| B18 | 2 |
| B29 | 2 |
| B30 | 2 |
| B31 | 2 |
| B32 | 1 |

The number of possible analogs to consider was reduced by narrowing the number of mutations in particular positions based on charge, size and hydrophobicity differences from the native amino acid at each position.

Positions A8 and A14. Relative to alternative substitutions, choice of Glutamic Acid at both positions A8 and A14 was preferred to co-optimize (a) the net negative charge of the insulin monomer or dimer at neutral pH, thereby enhancing solubility and electrostatic repulsion between monomers; (b) thermodynamic stability due to avoidance of an unfavorable beta-branched amino acid at A8 and an unfavorable reverse-hydrophobic effect at A14; and (c) prolongation of the fibrillation lag time in a zinc-free solution due to electrostatic repulsion between native or partially unfolded monomers, augmented thermodynamic stability and damped conformational fluctuations. $Glu^{A8}$ and $Glu^{A14}$ both reside in α-helical segments for which this amino acid has high intrinsic propensity. The two negative charges introduced in the A chain complement a net increase of three negative charges in the B chain (i.e., Glutamic Acids at positions B3 and B29, the latter in place of the basic side chain Lysine in wild-type human insulin).

"Site-2 Substitutions." In the absence of insulin, the free insulin receptor sits on cell surfaces like an upside-down horseshoe (∩) with the open end (the IR β-subunit) penetrating through the cell membrane and into the cell. When insulin binds to its receptor, a global change in IR quaternary structure occurs such that the two IR legs come together. Proximity of the transmembrane β-subunit α-helices then propagates to the intracellular tyrosine-kinase domains to trigger their autophosphorylation. WO 2013/110069, which is hereby incorporated by reference, proposed that interfering with the Site 2-interfacing residues of insulin could disrupt the duration of this autophosphorylation signal. To assess this, >1000 insulin tolerance tests were conducted in rats to assess the efficacy of mutations to the Site 2 residues on the duration of insulin activity in vivo.

Male Lewis rats (mean body mass ~300 g) were rendered diabetic by treatment with streptozotocin. Blood glucose values average 100 and 360 mg/dL in control and diabetic rats, respectively. Two rats (250-350 g body weight) were housed per cage and were unrestrained during the assay. To test the in vivo potency of a representative insulin analogue in relation to wild-type human insulin, protein solutions containing wild-type human insulin, the analogue to be assessed, or buffer alone (protein-free sterile diluent obtained from Lilly; composed of 16 mg of glycerin, 1.6 mg of meta-cresol, 0.65 mg of phenol, and 3.8 mg of sodium phosphate (pH 7.4) per ml) were injected intravenously, and the resulting changes in blood glucose were monitored by serial measurements using a glucometer. Assays were performed under fasting conditions (initiated in late AM following a 2 hr fast). Rats were injected into the tail vein at time t=0 with 10 μg of insulin in 100 μl of buffer per 300-g rat. Dose-response studies of wild-type insulin indicated that at this dose a near-maximal rate of glucose disposal during the first hour following injection. Blood was obtained from clipped tip of the tail at time 0 and every 10 min up to 90 min. >115 analogs were studied (with an average of n=8 rats) containing one (>35 analogs), two (65 analogs), or three (16 analogs) site-2 mutations.

The blood glucose time course for each animal was fit using (1) a Loess model and/or (2) a "4-phase" model consisting of contiguous linear segments: an "onset" segment, a horizontal "peak" segment (where the blood glucose drop was at or near maximum), a "first recovery phase" when blood glucose recovered quickly, and a "second recovery phase" when blood glucose returned more slowly toward pre-study levels. From the fit data, the following values were calculated both for each animal and for the average of the curves fit for animals exposed to the same test article: the slope of the onset curve, peak action (difference between the average blood glucose before the injection and the lowest blood glucose measured) and the duration of peak action (for 4-phase fits), time to peak action (time from when the injection was given to when peak action was observed), time to 50% recovery from peak action, and the slope of the first recovery curve. Statistics were calculated to determine which mutations or sets of mutations had a potential impact on shortening the duration of action of insulin. Based on these studies, the following mutations were eliminated as having a likely desired effect:

TABLE 3

Substitutions Eliminated after Site 2 Studies

| Position | Substitutions |
|----------|---------------|
| A13 | H, W |
| A17 | F, H, L |
| B17 | A, N |

Although studies in rats had suggested that classical "Site-2" substitutions (as defined in 1994 by DeMeyts and Schaffer) could (in some cases) lead to decreased duration of insulin signaling once the insulin receptor was engaged in targets tissues (see WO 2014/145593, which is hereby incorporated by reference in its entirety), such substitutions tended in vitro to decrease the stability of insulin and promote fibrillation. When the PD trends observed in rats failed to be observed in pigs, this category of substitutions was eliminated. A key advantage of such elimination was that the advantageous features elsewhere in the molecule (such as conferred, for example, by Glutamic Acid at positions A8 and A14 above) could be realized without offsetting penalties at Site-2 positions (as might arise due to the potential substitution of suboptimal side chains with respect to neighboring side-chain packing, decreased α-helical propensity, exposure of nonpolar surfaces or reduced electrostatic repulsion between insulin monomers).

N-terminal B-chain Segment. The N-terminal segment of human insulin (residues B1-B3) contributes to the foldability of proinsulin but is dispensable for the biological activity of the mature hormone. The native sequence Phe$^{B1}$-Val$^{B2}$-Asn$^{B3}$ is compatible with in vivo biosynthesis and subsequent steps: storage of the zinc hexamer in pancreatic beta-cells, and secretion and hormonal regulation of metabolism. The same sequence element is suboptimal, however, in a drug substance, as the dangling, disordered nonpolar side chains of Phe$^{B1}$ and Val$^{B2}$ contribute to fibrillation, and the side chain of Asn$^{B3}$ is prone to chemical degradation. To avoid these issues, an insulin analog may contain a combination of deletion and substitution in this segment. Removal of Phe$^{B1}$ eliminates a dangling aromatic ring whereas substitution of Valine by Alanine at B2 replaces a residue with preference for β-sheet by a residue with preference for α-helix. Substitution of Asn$^{B3}$ by Glutamic Acid enhances the net negative charge conferred above by Glutamic Acids at positions A8 and A14 to further increase solubility at neutral pH, enhance electrostatic repulsion between monomers and avoid pathways of chemical degradation open to Asp or Asn at B3. Deletion of residue B1 was preferred to deletion of residues [B1, B2] or B1-B3 to minimize the change from wild-type insulin and to avoid routes of chemical degradation open to Glutamic Acid or Glutamine at a neo-N terminus; the Alanine at position A2 provides a neutral spacer element between the alpha-amino group and functionalized side chains at B3 and B4. Alternatively, when residues B1 and B2 are deleted, residue B3 may be Ala, and when residues B1-B3 are deleted, residue B4 may be Ala.

Acidic B-Chain Tail. A two-residue extension of the B chain comprising Glutamic Acid at elongated positions B31 and B32 was considered as a means to introduce two negative charges in an effort to enhance solubility at neutral pH and increase the net negative charge of the protein, whether as a monomer, dimer or hexamer. An acidic C-terminal B-chain tail decreases cross-binding of insulin to the mitogenic Type 1 IGF-1 receptor (IGF-1R). However, such a tail may provide a neo-epitope, eliciting anti-insulin antibodies whose complexation could delay absorption from a subcutaneous depot or interfere with insulin action. Because of the net introduction of five negative charges elsewhere in the A- and B-chains (A8, A14, B3 and B29), it was not necessary to include additional B31-B32 negative charges to co-optimize solubility, physical stability and chemical stability; further, the Glutamic Acid at position B29 was sufficient to disfavor cross-binding to IGF-1R. Inclusion of the acidic B-chain tail would therefore have introduced antigenic risk without an offsetting advantage.

On the basis of such reasoning, the following mutations were eliminated:

This brought number of possible permutations down to about 2 million.

Expression, Purification and Stability

Insulin analogs are made commercially by biofermentation. Yeast or bacteria are modified genetically to produce insulin, then these cells are fermented in large tanks. The resulting media are then processed to extract and purify the insulin analog. Because insulin is a necessary medicine for so many, production costs are an important consideration. Therefore, an important criterion for selecting a candidate for clinical development is the ability to make the analogue at high yields. Initial efforts to ferment or purify certain two-chain insulin analogs led to elimination of analogues that contained a leucine or a valine at A21 or that contained an arginine at A17. This reduced the number of analogs to about 162,000. Physical and chemical stability studies performed using USP standards led the inventors to exclude analogs with a leucine at A14, reducing the field to about 86,400 analogs.

Gradient Descent

The remaining set of analogs represent in a 33-dimensional discrete state space (11 positions with 5, 3, 5, 2, 5, 3, 3, 2, 3, 2, and 2 possible discrete states respectively). An experimental plan was executed to rapidly search this space for analogs that maximized utility along a variety of metrics: stability, mitogenicity, cell-signaling, and pharmacodynamic performance. A set of 56 analogs was selected such that for each of the 11 positions being examined, there were at least three pairs of analogs where (a) each pair differed from each other by the same pair of residues but was otherwise the same (i.e., had the same "context") and (b) none of the pairs had the same context as each other. Each of these 56 analogs was synthesized and evaluated as follows:

TABLE 5

Experiments Done for Gradient Descent Analysis

| Experiment | Key Experimental Values Determined |
|---|---|
| 1. Related substances stability | Percent related substances |
| 2. High molecular weight protein (HMWP) stability | Percent covalent HMWP |
| 3. Fibrillation stability | Fibrillation lag time |
| 4. Insulin receptor activation (IR-A, IR-B) | Potency (EC$_{50}$) |
| 5. Insulin receptor deactivation time-course | Percent deactivation |

TABLE 4

Substitutions Eliminated by Structural Analysis

| Position | Substitutions | Why eliminated |
|---|---|---|
| A8 | R, N, D, C, G, L, K, M, F, P, S, Y, W | co-optimization of pI and stability |
| A12 | All | reassessment of "Site 2" substitutions |
| A13 | A, Q, Y | reassessment of "Site 2" substitutions |
| A14 | N, R, W | |
| A17 | A, N, W, Y | reassessment of "Site 2" substitutions |
| B1 | | Delete to remove dangling aromatic ring |
| B2 | V, E, Q | Substitute Ala to delay degradation/fib. |
| B3 | N, A, Q | Use Glu to enhance solubility, net charge |
| B13 | A, D, F, H, N, L, R, W, Y | reassessment of "Site 2" substitutions |
| B17 | H, Q, W, Y | reassessment of "Site 2" substitutions |
| B18 | L | reassessment of "Site 2" substitutions |
| B31 | E | Not needed for: |
| B32 | E | pI, solubility or IGF-1R selectivity |

This led to the following findings:

TABLE 6

| Optimal Substitutions Determined by Gradient Descent | | | | | | | |
| --- | --- | --- | --- | --- | --- | --- | --- |
| | A8 | A13 | A14 | A17 | B2 | B3 | B17 |
| Optimal RS | T or E | L | E | Q | A | A | L |
| Optimal HMWP | E | L | E | E | A | A or E | E |
| Optimal Fib | Q | L | A | Q | A | E | L |
| Optimal potency | H or E | L | — | — | — | — | — |

Based on these findings, the team eliminated the following mutations:

TABLE 7

| Position | Substitutions Eliminated by Gradient Descent Substitutions |
| --- | --- |
| A8 | T, A, H, Q |
| A13 | E, F |
| A14 | Y, A, Q |
| A17 | Q |
| B2 | E |
| B17 | E, F |

These studies reduced the space to about 160 possible analogs.

Design Optimization

Optimization of T-1123 molecular design expanded preferred sequences from the gradient descent studies to focus on 5 possible A21 mutations and 2 possible at position B13 to evaluate impact on chemical and physical stability. Evaluations were performed with 40 analogs including 2 different B1-B3 and B29-B30 designs and limited re-evaluation of 4 different mutations at the A8 position. More stringent stability and production yield criteria led to the selection of Gly at A21, maintenance of the native residue at B13, selection of desB1 AlaB2 and GluB3 as the optimal N-terminus combination, and selection of GluB29 over desB30 for the C-terminus. This narrowed the optimal sequence to the amino acid substitutions: GluA8 GluA14 GlyA21 desB1 AlaB2 GluB3 GluB29 (termed T-1123).

Runners-up included:

TABLE 8

| Potential Analogs Considered | |
| --- | --- |
| T-Code | Substitutions |
| T-1147 | GluA8 GluA14 GlyA21 desB1 AlaB2 AlaB3 GluB29 (SEQ ID NOS: 1 + 3) |
| T-1467 | GluA8 GluA14 ThrA21 desB1 AlaB2 GluB3 LysB28 (SEQ ID NOS: 4 + 5) |
| T-1470 | GluA8 GluA14 GlnA21 desB1 AlaB2 GluB3 GluB29 (SEQ ID NOS: 6 + 2) |
| T-1474 | GluA8 GluA14 AlaA21 desB1 AlaB2 GluB3 GluB29 (SEQ ID NOS: 7 + 2) |
| T-1488 | GluA8 GluA14 GlnA21 desB1 AlaB2 AlaB3 GluB29 (SEQ ID NOS: 6 + 3) |

Example 2: Multiplex Study of Insulin Analogs in Male Yucatan Miniature Swine Studies were conducted on male Yucatan miniature swine to determine pharmacokinetic (PK) profiles of various formulations of up to 5 non-potent insulin analogs following a single intravenous (IV) or multiple subcutaneous (SC)

administrations in castrated male Yucatan swine. The insulin analogues used for this example are "dead" analogues (defined previously as a type of nonalog) that do not bind to IR due to a modification of LeuA3, which is known in the art to nearly completely inhibit binding to IR.

In the IV phase of the study, dosing was intravenous with a single formulation containing all five inactive insulin analogs (Table 9). This was performed in the animal's normal housing. The dose was administered through one VAP which, after being flushed with ~6 ml of heparinized saline, was not used for PK blood sampling during the IV phase.

TABLE 9

| Examples of Nonalogs | |
| --- | --- |
| T-Code | Modifications |
| T-0068 | LeuA3 DesB30 (SEQ ID NOS: 8 + 9) |
| T-1069 | LeuA3 AlaB25 DesB30 (SEQ ID NOS: 8 + 10) |
| T-1071 | LeuA3 GlyB25 DesB30 (SEQ ID NOS: 8 + 11) |
| T-1072 | LeuA3 ValB25 DesB30 (SEQ ID NOS: 8 + 12) |
| T-1106 | LeuA3 LeuB25 DesB30 (SEQ ID NOS: 8 + 13) |

In the SC Phases of the study, dosing was subcutaneous with individual simultaneous injections of formulations of the analogs: each injection was of a different analogue, although the formulation of each analogue was in one instance the same and in another instance different. The animal was removed from its housing and restrained in a "V-trough" in a dorsal recumbent position to avoid exerting pressure on the injection sites. Whichever the dosing route, serial 3 ml blood samples were collected at designated time points for determination of blood glucose concentrations and plasma concentrations of the various analogs. Time 0=time of dose administration:

IV Phase: Pre-dose, 1, 2, 5, 10, 15, 30, 60, 120, 180, 240, 480, and 720 minutes post-dose SC Phase: Pre-dose, 1, 3, 5, 7, 10, 15, 20, 30, 45, 60, 90, 120, and 180 minutes post-dose Blood samples were collected into tubes containing the anticoagulant K2EDTA. Whole blood samples were processed within 30 minutes of collection. Plasma was processed by centrifuging at ~3,000 RPM for ~15 minutes at ~4° C. The resulting plasma was split evenly into two pre-labeled polypropylene cryovials (primary and backup), placed on dry ice and then stored frozen (approximately −70° C.).

Example 3: Detection and Quantification of Nonalogs in Plasma Samples

Nonalogs were isolated from mini pig plasma using a biotinylated monoclonal anti-insulin antibody derivatized to magnetic beads via a streptavidin coating on Sepharose paramagnetic beads. In brief, bioanalytical samples were thawed on ice, vortexed, transferred to deep well plates and spiked with the internal standard (IS), Lispro (USP). Lispro calibration, quality control, internal standards and nonalog plasma samples spiked with IS were mixed with biotinylated anti-insulin antibody-derivatized magnetic beads, centrifuged, covered and incubated with mixing. A liquid handling system was used to wash antibody-derivatized beads and to elute the internal standard and nonalogs from the beads. The eluates were transferred to a round bottom plate and stored at 4° C. until separation and detection using a hybrid liquid chromatography mass spectrometry system. Separation was achieved using a ultra-performance liquid chromatograph (UPLC) system equipped with thermostatted column compartment and autoinjector. All samples were separated using a C4 chemistry column and an aqueous mobile phase A and organic mobile phase B at 60° C. The separation occurred on a 10% to 40% mobile phase B gradient over 3 minutes. The nonalog was detected using a triple quadrupole mass spectrometer in positive ion mode with T-0068 detected at ion transitions of m/z 954.40136.10, T-1069 at 941.60136.10, T1072 at 946.40→136.10, T-1071 at 939.30→136.10 and Lispro internal standards detected using m/z 968.8→217.20 ion transitions. Samples were quantified using calibration curves developed using the peak area ratio method with weighted $1/x^2$ linear regression using Lispro as the internal standard.

Example 4: Pilot Studies

Pilot studies carried out in rats showed that the inactive insulin analogues in Example 3 were cleared from the bloodstream within 8 hours. This demonstrated that inactive forms of insulin analogues can be removed from the bloodstream efficiently without binding to insulin receptors.

Example 5: Analysis of Multiplex PK Studies Using Nonalogs

Figure 1:
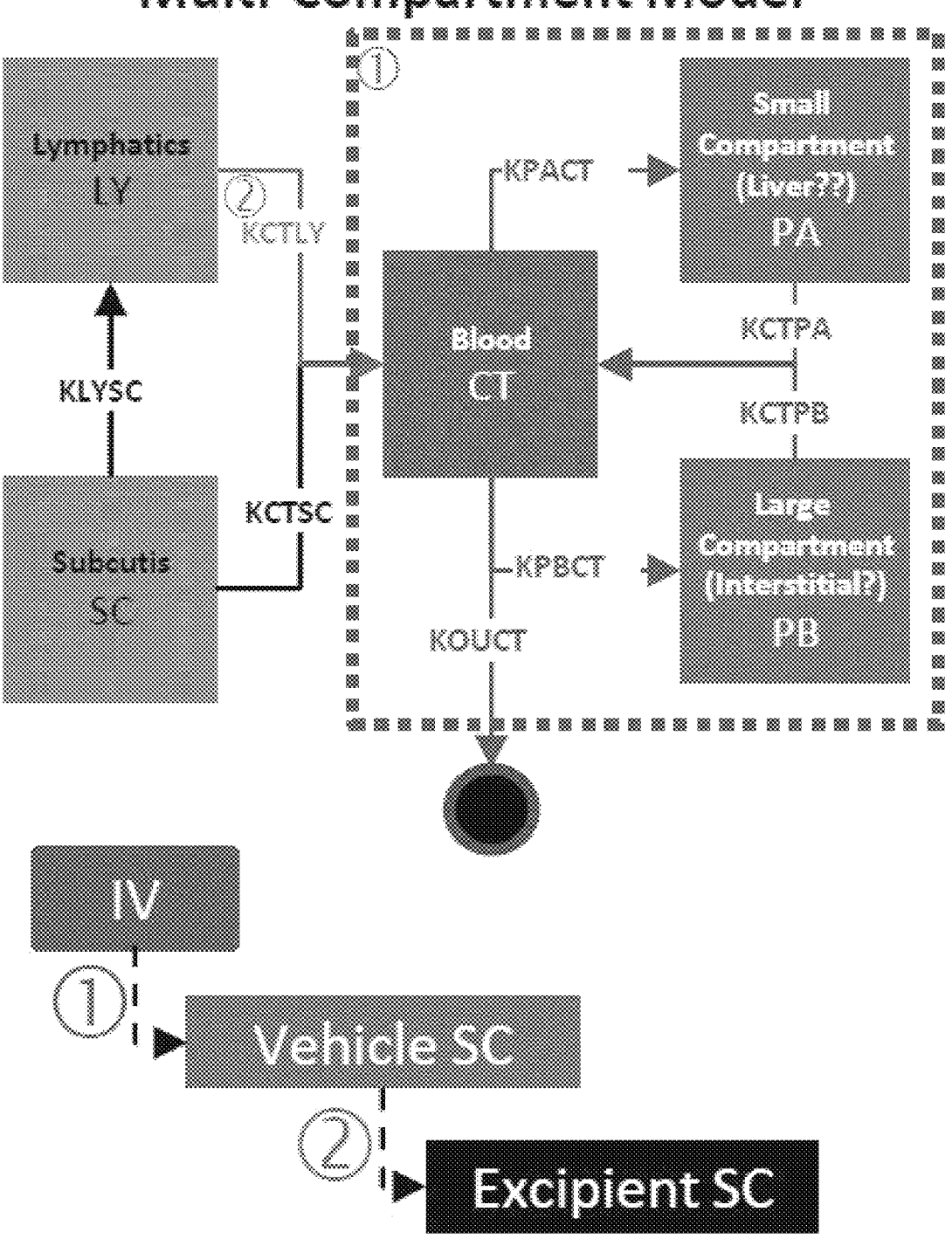
FIG. 1 shows a diagram summarizing the multi-compartmental flow model used to evaluate the results of pig multiplex pharmacokinetic studies.
Figure 2A:
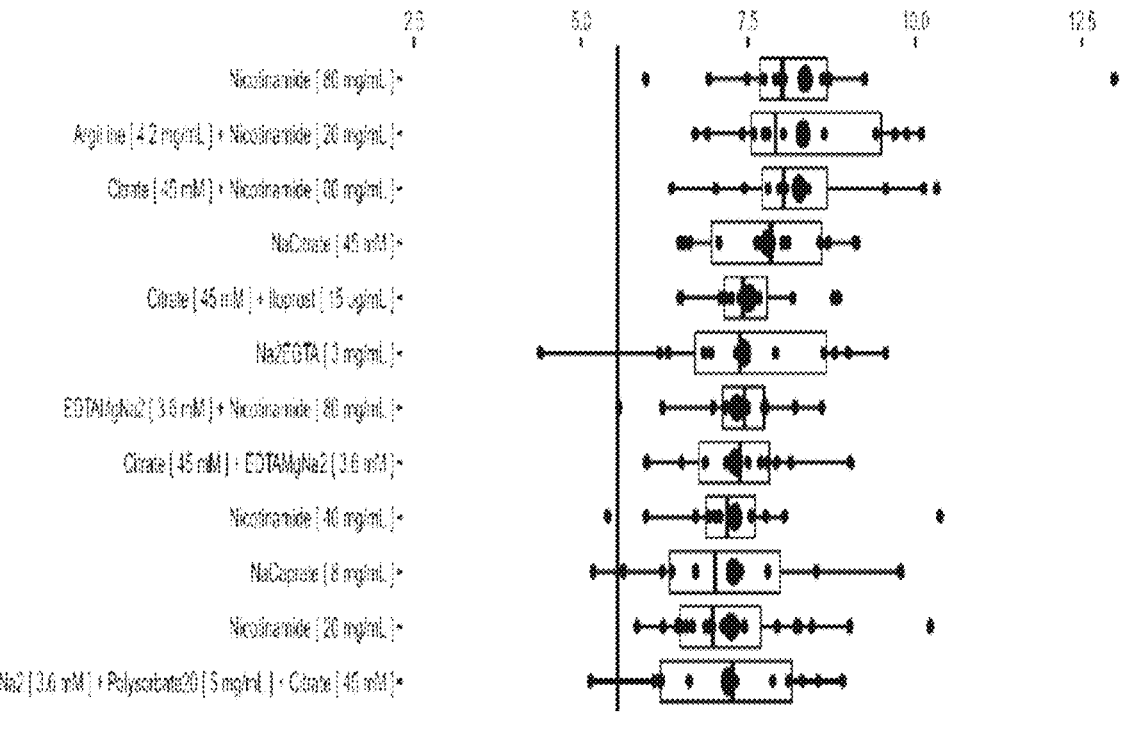
FIGS. 2A-2G show the results obtained from statistical analysis of multiplex PK studies for Formulation Screening. Graphical depiction of onset slopes of PK response in swine injected subcutaneously with formulations (of a surrogate insulin analog) containing a multitude of candidate accelerating excipients. Each column is a unique formulation with the individual animals shown as black dots and the average shown as empty or filled dots. Filled dots are statistically different than the control (highlighted by an arrow at the bottom of the figure and for comparison to each trial as the line in the middle of the figure) whereas empty dots are not different that the control. If a filled dot is to the right of the vertical line that intersects the whole of the figure, the insulin analogue is absorbed statistically faster than control, and if it is to the left of the vertical line, it is absorbed statistically slower than the control.
Figure 2B:
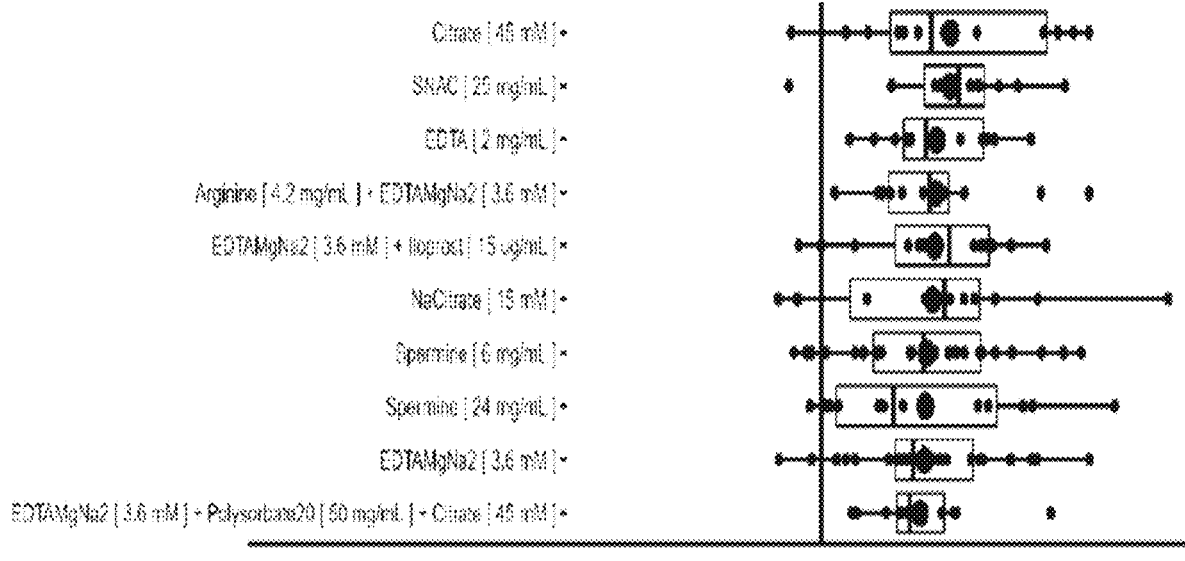
Figure 2C:
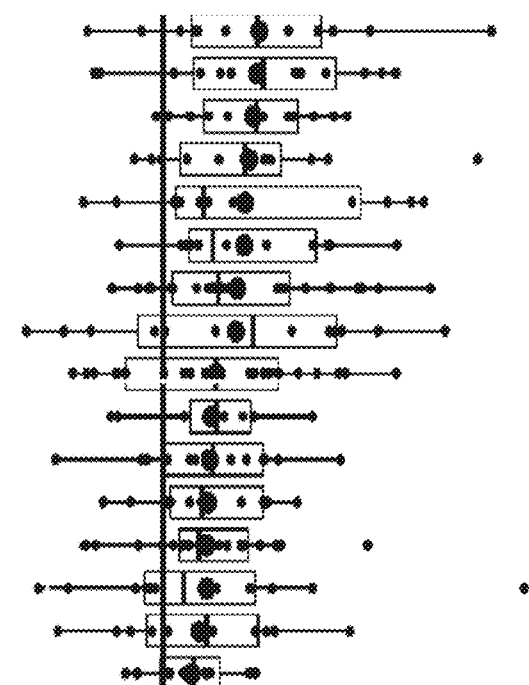
Figure 2D:
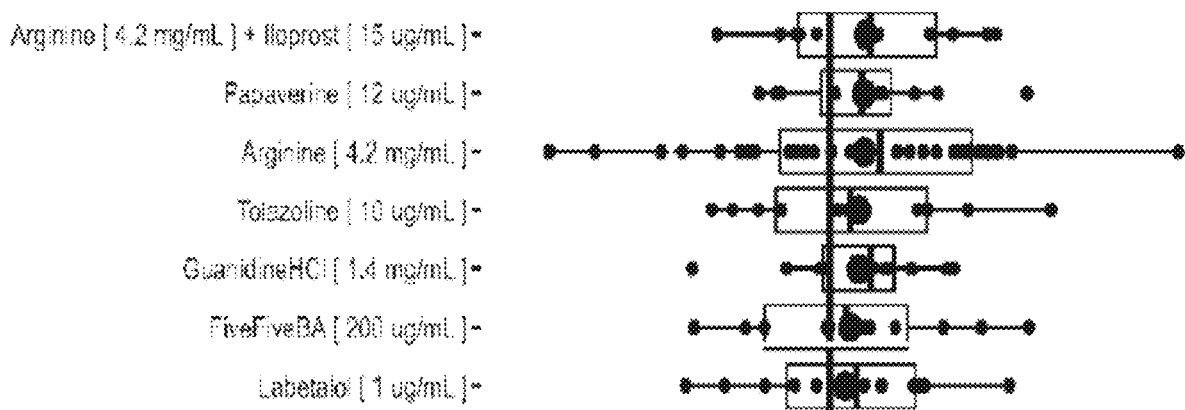
Figure 2E:
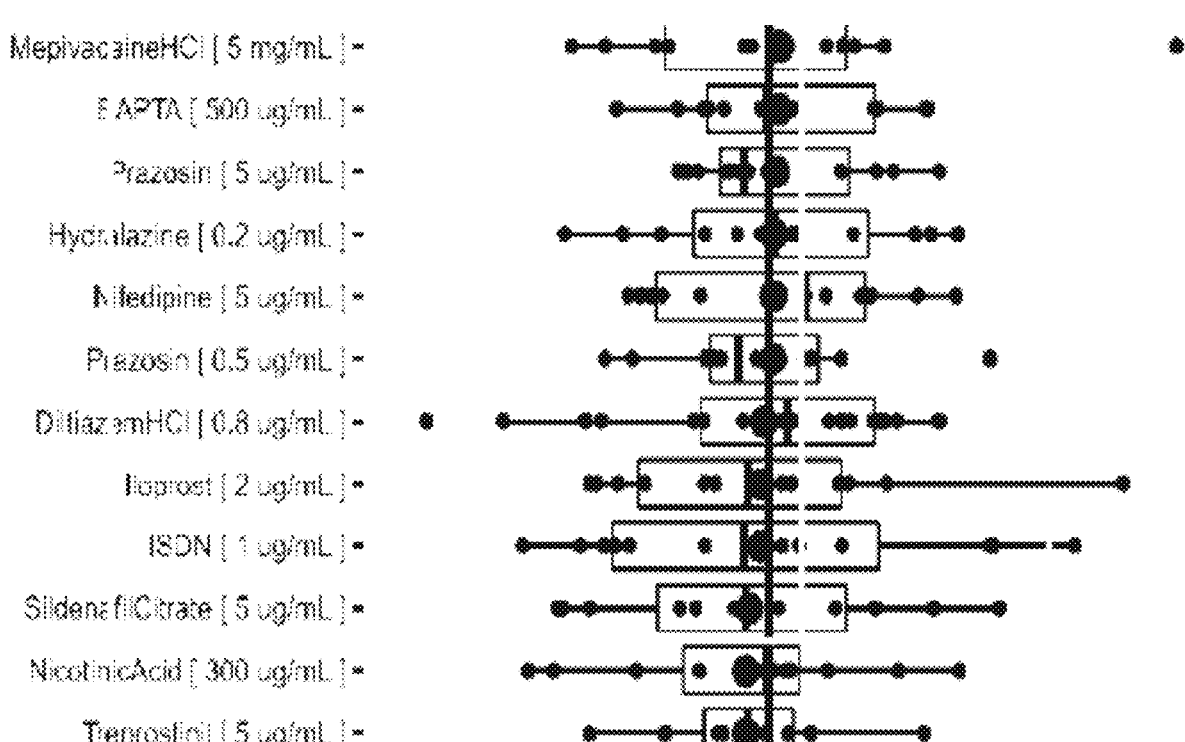
Figure 2P:
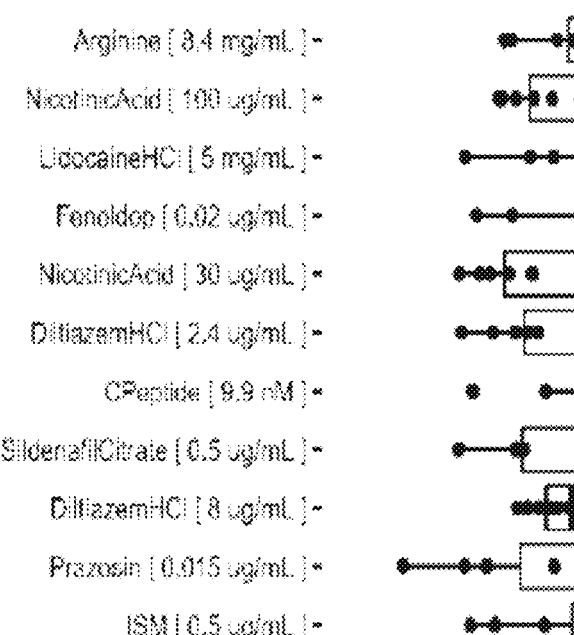
Figure 2P:
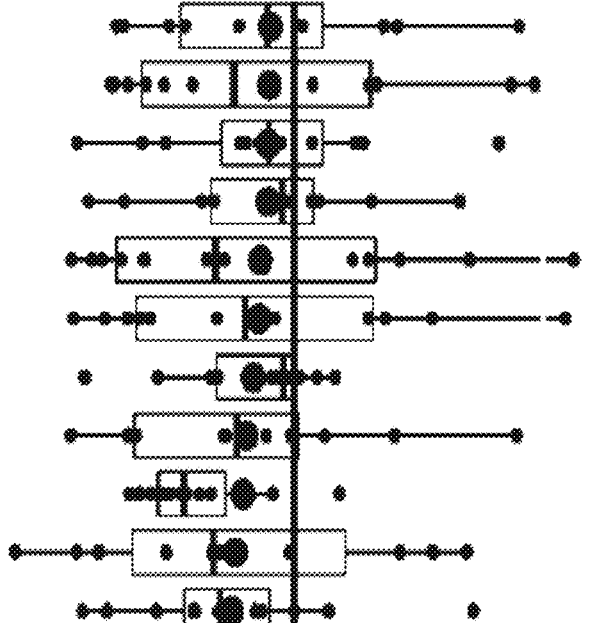
Figure 2G:
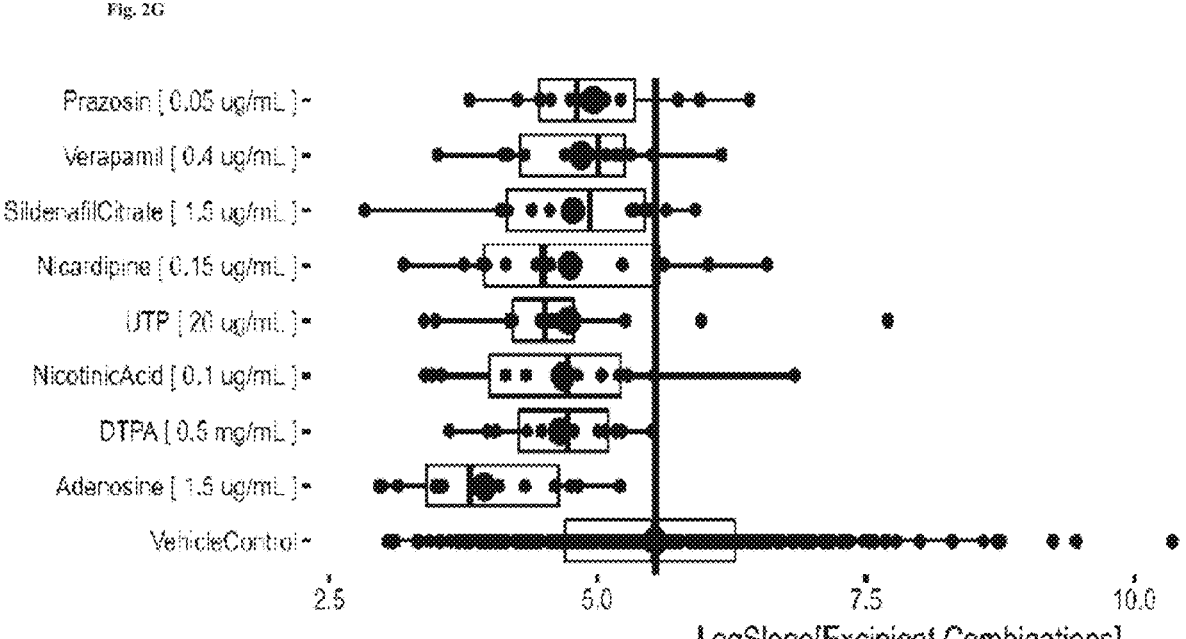

Data from the IV and SC studies in Example 2 were merged into a single database and analyzed as follows. A multi-compartment model of insulin action was developed (FIG. 1) that identified five separate compartments: (1) The subcutaneous (SC) space into which the injection is initially made, (2) the lymphatic system (LY) that takes up some of the insulin and ultimately delivers it to the blood system), (3) the blood system, which is also called the central compartment (CT) that takes up the rest of the insulin from the SC, (4) a large processing compartment (PB) that receives and metabolizes insulin but returns some to CT, and (5) a small processing compartment (PA) that also receives, metabolizes and returns insulin to CT. The model also has a route of elimination (OU) without metabolism (i.e., kidney elimination from the CT). The model is represented by a series of partial differential equations (based on standard intercompartmental flow equations) on the variables representing insulin concentrations within—and the flows between—the compartments as functions of time.

First, the pharmacodynamics of the nonalogs post absorption into the CT was analyzed utilizing the data from the IV experiments. Parameters for a reduced, post-CT model (excluding SC and LY) were fit to the data from the IV studies utilizing numerical methods. From this it was determined that the half-life of the nonalogs in pigs was on the order of 8 hours (compared to 5 minutes for potent insulin analogs).

It should be noted that the analysis described above is not the only analytical approach possible. While the elimination parameters above were fixed by IV pre-evaluations and considered as constant across subjects and across nonalogs, in reality, the elimination parameters probably vary by subject (and possibly by nonalog). Also, this design only provides one or two time points for characterizing the tails of the PK curves. If more sampling time points on the tails of PK curves had been included, the assumption that the elimination parameters are constant could have been removed.

Once these post-CT parameters were determined, they were fixed as constants in the full model, and data from each SC experiment were fit to this larger model in order to determine SC→LY, SC→CT, and LY→CT flow parameters for each SC experiment. An absorption model for each SC experiment was then determined by utilizing the parameters calculated for the pre-CT flows and setting the post-CT flows to zero. From this absorption model, certain empirical absorption metrics were obtained (e.g., absorption rate over the first 30 minutes, the maximum slope of absorption, and the area under the absorption curve (AUC)). These empirical absorption metrics from each SC experiment were then used to evaluate the impact of different excipients on absorption.

A mixed effects model was utilized to isolate the effect of specific excipients on absorption metrics, controlling for variables such as nonalog elimination, pig variability, and different experiment days. The results identified the magnitude and significance of the impact of excipients or excipient cocktails on absorption. These results were used to identify the most promising excipients and cocktails to be evaluated in euglycemic clamps.

Example 6: Formulation Design

A series of studies based on the methods described in Examples 2, 3, 4, and 5 was used to determine the optimal excipients to use in the insulin composition, and at what concentrations.

FIG. 2 shows the results obtained from statistical analysis of multiplex PK studies for Formulation Screening.

The pharmacodynamic properties of various T-1123 formulations were investigated in a Yucatan minipig model. On the day of study, to block endogenous pancreatic α- and β-cell secretion, pigs were given an intravenous bolus of octreotide acetate (7.2 μg/kg) approximately 60 min before beginning the clamp study, followed immediately by an intravenous maintenance infusion of 3.6 μg/kg/hr until the conclusion of the clamp. After baseline euglycemia was established with 10% dextrose infusion, a subcutaneous injection of 1.35 nmol/kg T-1123 formulations, 1.35 nmol/kg Fiasp, or diluent was given into the abdomen. In order to quantify peripheral insulin-mediated glucose uptake, a variable-rate glucose infusion was given to maintain a blood glucose concentration of approximately 85 mg/dl over the duration of insulin action, typically 4-6 hours. Glucose Consumption (GC) is a measure of insulin action during a euglycemic clamp. It is different from Glucose Infusion Rate (GIR) because it takes into consideration changes in blood glucose (BG) levels. This is important because clamping protocols are imperfect and BG fluctuates when actual insulin action is different from that predicted at the beginning of a time period when GIR is set. GC between time t1 and time t2 is calculated as GIR (between t1 and t2)–(BG (t2)~BG(t1))*Vd/(t2–t1) where Vd is the "Volume of Distribution" (i.e., the volume of blood in the subject). The units for GIR are mg/min. Units for BG in the United States is mg/dL. Units for Vd are dL. Units for t1 and t2 are min.

Fitted GC curves were used to calculate the following parameters: time to half-maximal effect (early), time to half-maximal effect (late), time to maximal effect, and area-under-the-curve (AUC) over baseline.

Figure 3:
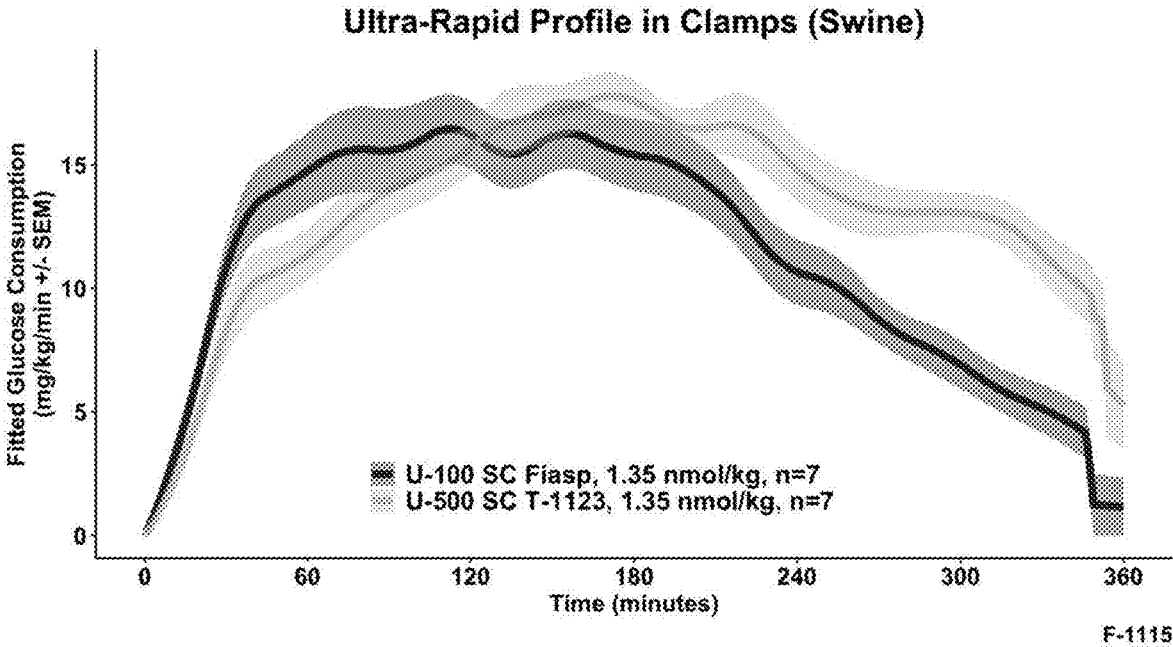
FIG. 3 shows the results obtained from euglycemic clamp studies showing the glucose infusion rate needed to maintain euglycemia (n=7) over 360 minutes after non-diabetic Yucatan pigs were dosed subcutaneously with either U-100 Fiasp or U-500 T-1123 in base formulation.

When compared to U-100 Fiasp, U-500 T-1123 in base formulation (Table 10) consisting of neutral buffer, preservative and tonicity agent, shows similar potency and onset of action. In contrast, U-500 T-1123 in base formulation exhibits prolonged tail of action compared to U-100 Fiasp (FIG. 3).

Several absorption-enhancing excipients identified through the multiplex PK studies outlined in FIG. 2 were tested in U-500 T-1123 formulations to compare to U-100

Figure 4:
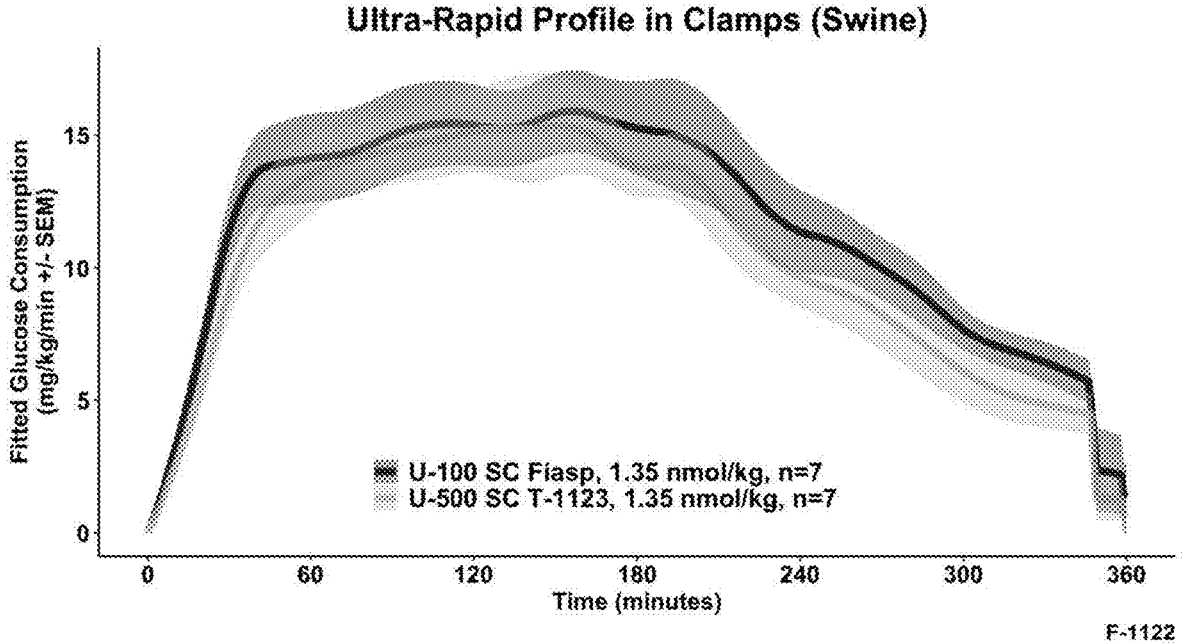
FIG. 4 shows the results obtained from euglycemic clamp studies showing the glucose infusion rate needed to maintain euglycemia (n=7) over 360 minutes after non-diabetic Yucatan pigs were dosed subcutaneously with either U-100 Fiasp or U-500 T-1123 in accelerated formulation.
Figure 5:
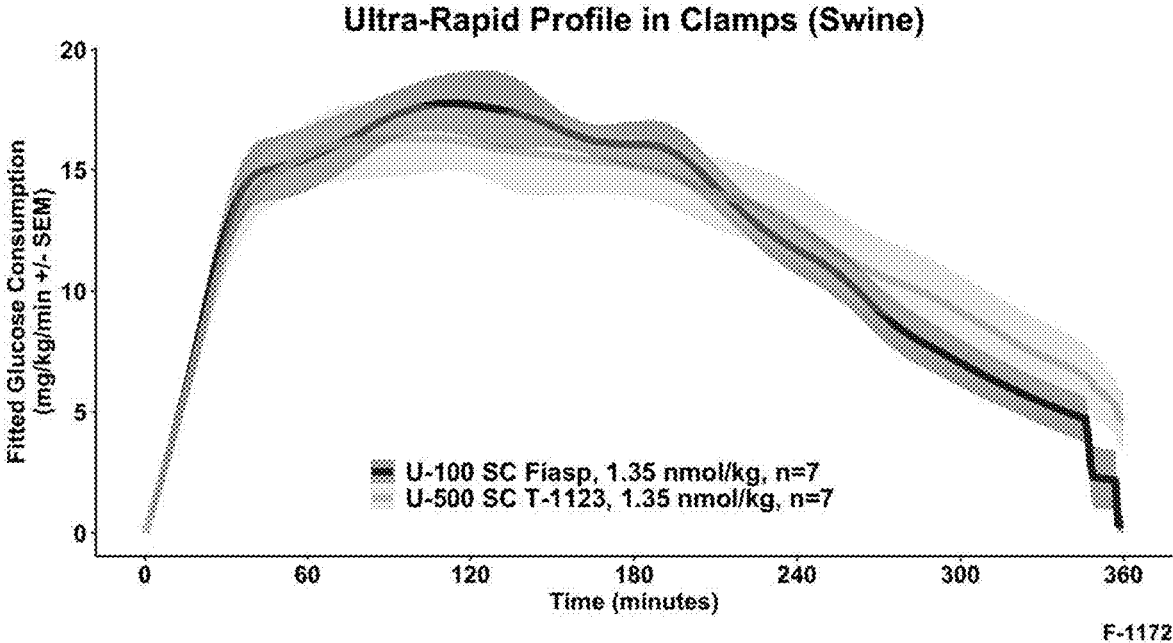
FIG. 5 shows the results obtained from euglycemic clamp studies showing the glucose infusion rate needed to maintain euglycemia (n=7) over 360 minutes after non-diabetic Yucatan pigs were dosed subcutaneously with either U-100 Fiasp or U-500 T-1123 in accelerated formulation optimized for stability.

Fiasp. A combination of three active excipients (citrate, EDTA, iloprost) was demonstrated in U-500 T-1123 (accelerated formulation) to match the time action profile and pharmacodynamic properties of U-100 Fiasp with non-significant difference for onset and tail of action (FIG. 4). A further modification of this formulation (U-500 T-1123 in accelerated formulation optimized for stability), exhibited equivalent potency AUC, onset, and Tmax with a slightly longer tail of action (FIG. 5).

TABLE 10

| | U-500 T-1123 ultra-rapid formulations | | | | | | |
|---|---|---|---|---|---|---|---|
| TA | iloprost (µg/ml) | EDTA (mM) | Mg$^{++}$ (mM) | Glycerin (mg/ml) | m-Cresol (mg/ml) | Citrate (mM) | Tris (mM) |
| U-500 T-1123 in base formulation | 0 | 0 | 0 | 16 | 3.2 | 0 | 50 |
| U-500 T-1123 in accelerated formulation | 15 | 6.2 | 6.2 | 16 | 3.2 | 45 | 0 |
| U-500 T-1123 in accelerated formulation optimized for stability | 15 | 6.2 | 0 | 16 | 3.2 | 45 | 10 |

Once the set of optimal excipients was determined, PD studies were conducted in pigs with variant T-1123 formugreatly prolonged tail of increased glucose consumption towards the end of the study. PD metrics are summarized in Table 12. Taken together, these studies show that Tris, EDTA, and iloprost provide a good PD profile for a T-1123 composition.

TABLE 11

| | U-500 T-1123 subtractive formulations | | | | | | |
|---|---|---|---|---|---|---|---|
| TA | iloprost (µg/ml) | EDTA (mM) | Mg$^{++}$ (mM) | Glycerin (mg/ml) | m-Cresol (mg/ml) | Citrate (mM) | Tris (mM) |
| U-500 T-1123 minus citrate | 15 | 6.2 | 6.2 | 16 | 3.2 | 0 | 50 |
| U-500 T-1123 minus EDTA | 15 | | 6.2 | 16 | 3.2 | 45 | |
| U-500 T-1123 minus iloprost | | 6.2 | 6.2 | 16 | 3.2 | 45 | 10 |

TABLE 12

Figure 6A:
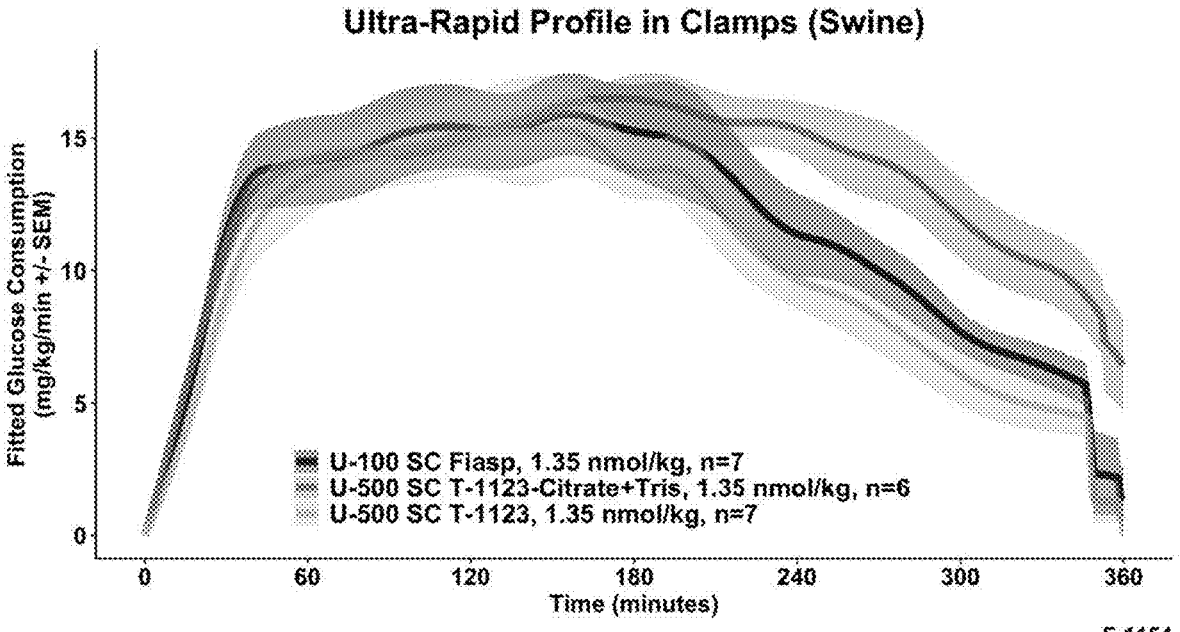
FIG. 6A-C summarizes the results obtained from euglycemic clamp studies showing the glucose infusion rate needed to maintain euglycemia (n=7) after the pigs were treated with either U-100 Fiasp or U-500 T-1123 subtractive formulations.
Figure 6B:
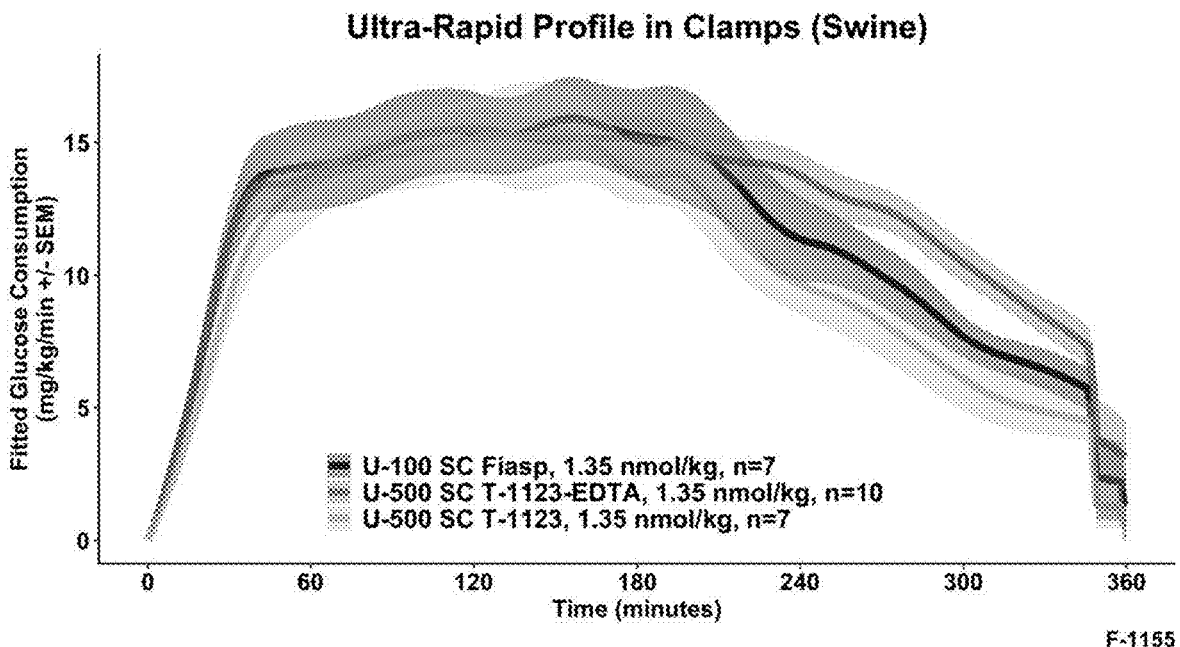
Figure 6C:
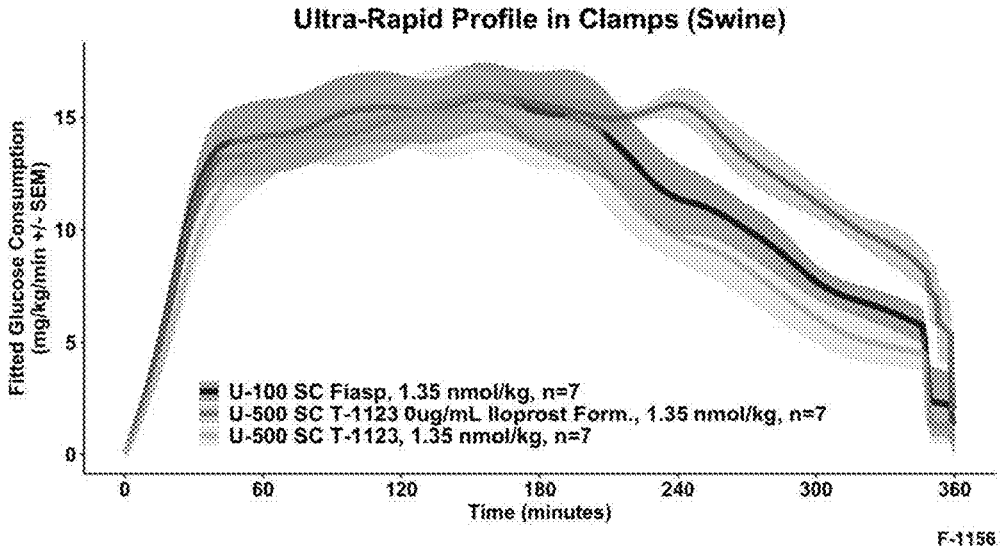

| | U-500 T-1123 subtractive formulations pig PD metrics (SE in parentheses) | | | | | | | |
|---|---|---|---|---|---|---|---|---|
| TA | n | AUC First 30 Minutes (%) | AUC After 180 Minutes (%) | Onset (Minutes) | Time to Max GC (Minutes) | Offset (Minutes) | AUC (mg/kg/min) | Max GC (mg/kg/min) |
| U-100 SC Fiasp, 1.35 nmol/kg | 7 | 3.81 (0.42) | 42.03 (2.77) | 22.64 (2.19) | 135.28 (20.31) | 297.00 (18.77) | 4170.27 (401.26) | 17.65 (1.53) |
| U-500 SC T-1123 minus citrate, 1.35 nmol/kg | 6 | 3.42 (0.29) | 50.34 (2.47) | 20.83 (2.65) | 180.33 (21.54) | 346.83 (12.35) | 4913.03 (274.4) | 17.46 (0.76) |
| U-500 SC T-1123 minus EDTA, 1.35 nmol/kg | 10 | 3.55 (0.2) | 46.69 (1.18) | 20.00 (1.14) | 137.80 (16.45) | 343.25 (6.87) | 4483.46 (217.02) | 16.70 (0.61) |
| U-500 SC T-1123 minus iloprost, 1.35 nmol/kg | 7 | 3.36 (0.2) | 49.06 (2.14) | 20.64 (1.6) | 187.85 (20.37) | 344.7 (8.8) | 4609.18 (167.98) | 18.07 (0.93) | lations with specific excipients subtracted (Table 11). These subtractive analysis studies ensured that each active component of the formulation was necessary to achieve optimal PD parameters. In FIGS. 6A, 6B, and 6C, citrate was replaced with Tris, EDTA was removed, and iloprost was removed, respectively. When citrate was replaced with Tris (FIG. 6A), the time to max glucose consumption in the pigs was increased, and there was a prolonged tail of increased glucose consumption towards the end of the study. When EDTA was removed from the formulation (FIG. 6B), there was a prolonged tail of increased glucose consumption towards the end of the study. When iloprost was removed from the formulation (FIG. 6C), the time to max glucose consumption in the pigs was increased, and there was a Example 7: Effect of Iloprost on Fibrillation Lag Time Insulin analogues (Humalog®, T-1123) formulated according to Table 13 were evaluated for fibrillation lag time determined through an accelerated Thioflavin T (ThT) dye assay. The formulations were tested in triplicate in an accelerated fibrillation assay at 40° C. with agitation. Briefly, 250 µL of formulated samples were added to the 96 well plate such that each well contained 5 µM Thioflavin T (ThT). Fluorescence data was acquired every 20 minutes at an emission wavelength of 480 nm after excitation at 440 nm. The plate reader was held at 40° C. for 7 days with continuous cycling of 30 second linear agitation (1000 cpm)

and 30 second rest. The mechanism by which ThT dye indicates amyloid fibrils is that the ThT dye binds with the beta sheet structure of fibrils as fibrillation occurs, and its emission intensity steadily increases. Fibrillation lag time is a measure of time taken by insulin or an analogue thereof to begin to form fibrils. For the purposes of this disclosure, fibrillation lag time is determined by linear regression of the slope of the fitted curve of the emission spectra to the x-axis (time).

TABLE 15-continued

| Iloprost does not extend fibrillation lag time of insulin lispro | | | | |
|---|---|---|---|---|
| TA | Formulation | Replicates | Mean lag time (hr) | SD (hr) |
| Humalog | Commercial Humalog + 15 µg/ml iloprost | 3 | 8.97 | 2.07 |

TABLE 13

| U500 T-1123 Fibrillation Formulations | | | | | | | |
|---|---|---|---|---|---|---|---|
| TA | iloprost (µg/ml) | EDTA (mM) | Mg++ (mM) | Glycerin (mg/ml) | m-Cresol (mg/ml) | Citrate (mM) | Tris (mM) |
| U-500 T-1123 in base formulation | 0 | 0 | 0 | 16 | 3.2 | 0 | 50 |
| U500 T-1123 in base formulation + iloprost | 15 | 0 | 0 | 16 | 3.2 | 0 | 50 |
| U-500 T-1123 in citrate formulation + iloprost | 15 | 6.2 | 6.2 | 16 | 3.2 | 45 | 0 |
| U-500 T-1123 in citrate formulation + Tris | 15 | 6.2 | 6.2 | 16 | 3.2 | 45 | 10 |

T-1123, when formulated with buffer, preservative, and tonicity agent, ("base formulation") had a fibrillation lag time (25.1 hr) markedly higher than Humalog (7.47 hr) (Table 14, FIG. 7A). Surprisingly, the addition of iloprost to the same formulation tremendously increased the fibrillation lag time of T-1123 to 168+hr an over six-fold increase. The increase in fibrillation lag time remained, when Tris was replaced by the buffering agent citrate and when Tris and citrate were used in combination. Prior to the described observation there was no indication that iloprost would have notable characteristics as a stabilizing excipient.

TABLE 15-continued

| Iloprost does not extend fibrillation lag time of insulin lispro | | | | |
|---|---|---|---|---|
| TA | Formulation | Replicates | Mean lag time (hr) | SD (hr) |
| Humalog | Commercial Humalog + 50 µg/ml iloprost | 3 | 9.90 | 1.36 |
| Humalog | Commercial Humalog + 100 µg/ml iloprost | 3 | 9.45 | 3.59 |

TABLE 14

| Iloprost extends fibrillation lag time of T-1123 | | | |
|---|---|---|---|
| TA | Replicates (n) | Mean lag time (hr) SD (hr) | Comments |
| Humalog | 6 | 7.47 | 1.89 | |
| U-500 T-1123 in base formulation | 11 | 25.1 | 5.59 | |
| U-500 T-1123 in base formulation + iloprost | 3 | 168 | 0 | Did not fibrillate in 168 hrs |
| U-500 T-1123 in citrate formulation + iloprost | 6 | 168+ | 0 | Did not fibrillate in 168 hrs |
| U-500 T-1123 in citrate formulation + iloprost + Tris | 15 | 168+ | 0 | Did not fibrillate in 168 hrs |

Next, the protective effect of iloprost against fibrillation was tested in a commercially available insulin analogue. Fibrillation lag time was evaluated in Humalog with 3 increasing concentrations of iloprost, according to the method described above. Iloprost had only a slight effect on the fibrillation lag time of Humalog at the iloprost concentrations tested (Table 15).

TABLE 15

| Iloprost does not extend fibrillation lag time of insulin lispro | | | | |
|---|---|---|---|---|
| TA | Formulation | Replicates | Mean lag time (hr) | SD (hr) |
| Humalog | Commercial Humalog + 0 µg/ml iloprost | 6 | 7.47 | 1.89 |

T-1123 formulations demonstrating time-action profiles equivalent to Fiasp (Example 6, Table 10) were evaluated for physical stability performance in the accelerated fibrillation assay using ThT fluorescence. U-500 T-1123 formulations containing 15 ug/mL iloprost did not fibrillate in 168 hours (Table 14), while U-500 T-1123 in base formulation without iloprost fibrillated in 25.10±5.59 hours and commercial Humalog fibrillated in 7.47±1.89 hours (Table 15).

Example 8: Chemical and Physical Stability of T-1123

The chemical stability of U-500 T-1123 formulated in base formulation (Table 10) was compared to commercially available U-100 Humalog and U-500 Humulin using RS and HMWP, and fibrillation as in Example 7. To determine RS and HMWP, U-500 (17.5 mg/ml) zinc-free formulations of insulin analogues, U100 Humalog, and U500 Humulin were heat stressed at 40° C. for 28 days. RS were characterized by reverse phase UPLC and LC-MS. HMWP formation as covalent dimers and oligomers was quantified by size exclusion high performance liquid chromatography (SEC-HPLC). After the incubation period, T-1123 in base formulation showed chemical degradation due to RS and HMWP at levels similar to U-100 Humalog and U-500 Humulin (FIG. 8A). Across all three compositions tested, no more than 3% purity was lost over the course of the study. U-500 T-1123 exhibited slightly improved RS as compared to U-100 Humalog and slightly improved HMWP as compared to U-100 Humalog and U-500 Humulin.

Long-term studies were also performed to evaluate the chemical and physical stabilities of T-1123. For these studies, U500 T-1123 was formulated in citrate formulation with Tris as described in Table 13, then placed in vials on a nutator at 30° C. for one year. RS for T-1123 showed only a 3.14% decline under these conditions after one year (FIG. 8F). Also, none of the test samples had fibrillated, in contrast to commercial formulations of U400 Insuman (fibrillation at 81 days) and U100 Humalog (fibrillation at 32.75 days) (FIG. 7D).

Example 9: Chemical Stability Optimization of T-1123 Ultra-Rapid Formulations Titrations were performed in iterations of excipients to determine optimal combinations and concentrations for use in the formulation development of T-1123. All test formulations contained 45 mM sodium citrate, 6.2 mM EDTA (various salts), 15 μg/mL iloprost, and 0.32% m-cresol at U-500 T-1123 concentration. Formulations of insulin analogues were heat stressed at 45° C. for 7 days and RS and HMWP characterized as described in Example 8. Exemplary studies are shown in FIGS. 8B-8E. FIGS. 8B and 8C summarize the effect magnesium and Tris have on the chemical stability of T-1123. At non-equimolar concentrations of EDTA/$Mg^{2+}$, there is a direct correlation between API purity and increasing concentrations of Tris, indicating improved stability. FIGS. 8D and 8E summarize the effect of glycerin and Tris titrations at 4 mM $Mg^{2+}$. Increasing concentrations of Tris and glycerin decrease HMWP generation and this effect is maximized at 20 mM Tris, and 20 mg/mL glycerin.

Results of further chemical degradation studies are provided in FIG. 8F. T-123 compositions were formulated as shown in Table 16. FIG. 8F shows losses in purity due to due to accumulation of Related Substances (RS) and covalent High Molecular Weight Protein (HMWP) for select formulations STA-0067 (n=3), STA-0109 (n=3), and STA-0116 (n=2).

TABLE 16

| U500 T-1123 formulations in various concentrations of Mg+, Glycerin and Tris | | | | | | | |
|---|---|---|---|---|---|---|---|
| Formulation | Citrate (mM) | Iloprost (ug/mL) | Na2-EDTA (mM) | MgSO4 (mM) | Glycerin (mg/mL) | m-cresol (%) | Tris (mM) |
| STA-067 | 45 | 15 | 6.2 | 6.2 | 16 | 0.32 | 10 |
| STA-109 | 45 | 15 | 6.2 | 4 | 13 | 0.32 | 10 |
| STA-116 | 45 | 15 | 6.2 | 5 | 13 | 0.32 | 12 |

Example 10: Aggregation of T-1123 Formulations

The self-association status of T-1123 was investigated at a protein concentration of 3.0 mM in Zn free formulation containing m-cresol and glycerin in Tris buffer, pH 7.4 by dynamic light scattering (DLS) using a Wyatt Dynapro plate reader III (Wyatt Technology). U-500 T-1123 Zn-free formulated samples and commercial samples of U-100 Humalog and U-500 Humulin R were monitored for changes in aggregation state at 40° C. for 28 days. For in situ measurements, autocorrelation functions of scattered light were collected using 10 acquisitions (5 sec per acquisition) and converted into particle-size distributions using the "regularization" size distribution and Rayleigh spheres model. The aggregation state of Zn-free U-500 T-1123 was unchanged with heat stress for the course of the study. Analysis of the scattering data revealed that T-1123 was predominantly dimeric under these conditions whereas the estimated average molecular weight of U-100 Humalog and U-500 Humulin R was that expected for an insulin hexamer at t=0 min and U-500 Humulin R showed significant further increase in mean molar mass (i.e. exceeding hexamer) over the course of the study. Ultra-rapid formulations of T-1123 described in Table 17 were assessed for change in aggregation state in response to heat stress (40° C. for 28 days) as above and were demonstrated to be unchanged over the course of the study.

TABLE 17

| U-500 T-1123 ultra-rapid formulations demonstrate extended lag time | | | | | | | | |
|---|---|---|---|---|---|---|---|---|
| TA | iloprost (μg/ml) | EDTA (mM) | $Mg^{++}$ (mM) | Glycerin (mg/ml) | m-Cresol (mg/ml) | Citrate (mM) | Tris (mM) | Mean lag time (hr) | n |
| U-500 T-1123 in accelerated formulation | 15 | 6.2 | 6.2 | 16 | 3.2 | 45 | | 168+ | 3 |
| U-500 T-1123 in accelerated formulation optimized for stability | 15 | 6.2 | | 16 | 3.2 | 45 | 10 | 168+ | 3 |

Example 11: Cell-Based Assays

In vitro potency of T-1123 relative to human insulin was determined in cell-based receptor activation assays that quantify tyrosine phosphorylation, including of the insulin receptor, in CHO cells overexpressing the A (hIR-A) or B (hIR-B) isoforms of the human insulin receptor. Increase in tyrosine phosphorylation was measured using In Cell Western kit (LICOR) using anti-pTyr primary antibody 4G10 (Millipore) after insulin stimulation. Results were normalized for cell number using DNA quantification. Dose response data were fitted with a four-parameter logistic model to determine $EC_{50}$ values. Human insulin receptor (isoform A; hIR-A) activation for T-1123 and HI exhibited respective $EC_{50}$ values of 23.2±1.28 and 10.5±2.28 nM; similarly, respective hIR-B activation $EC_{50}$ values were 3.7±0.13 and 2.6±0.11 nM. The relative potency of T-1123 in the IR activation assay is consistent with full potency in vivo relative to HI.

The dephosphorylation kinetics of T-1123 and HI were assessed through In-Cell Western (LICOR) quantification of the decrease in tyrosine phosphorylation after washout of insulin stimulation. Dephosphorylation assays were conducted in CHO cells overexpressing the hIR-A or hIR-B receptor. The CHO cells were stimulated with T-1123 or HI at a fixed concentration of 100 nM for 5 minutes and then washed to remove the insulin. At five time points following the washout (0, 30, 60, 120 and 180 mins) tyrosine phosphorylation was measured using In Cell Western kit (LICOR) using anti-pTyr primary antibody 4G10 (Millipore). Results were normalized for cell number using DNA quantification. Duration of signaling for T-1123 in hIR-A and hIR-B cells was less than or equal to HI (FIG. 9A, FIG. 9B) indicating mitogenic risk potential no greater than HI.

The metabolic potency of T-1123 was assessed in an anti-lipolysis assay using differentiated human preadipocytes. Preadipocyte cells were differentiated with DM-2 Subcutaneous Preadipocyte Differentiation Medium (Zen-Bio) in a 96-well plate for 14 days. Differentiated cells were stimulated with isoproterenol (0.5 nM) to stimulate lipolysis that can be measured as glycerol released into the cell culture medium. Lipolysis was suppressed by a dilution series of HI or T-1123 for 4 h. The cell culture media were transferred to a new 96-well plate, and the release of glycerol was measured by a 3-step process that ultimately produces a quinoeimine dye with absorbance at 540 nm. Glycerol release dose response data were fitted with a four-parameter logistic model to determine $EC_{50}$ values for inhibition; 0.54±0.14 nM and 0.56±0.15 nM for T-1123 and HI, respectively. The indistinguishable potencies of T-1123 versus HI in the anti-lipolysis assay is consistent with full metabolic potency of T-1123.

The mitogenic potential of T-1123 was assessed by $[2-^{14}C]$-thymidine incorporation in cell proliferation assays using human breast cancer-derived MCF-7 cells. Serum starved cells were stimulated with a dilution series of T-1123 or HI control at 10 pM to 1500 nM and incubated overnight followed by 6-hour incubation with $[2-^{14}C]$-thymidine solution. Incorporation of $[2-^{14}C]$-thymidine was measured with a scintillation counter and dose-response curves calculated from n=8 technical replicates. T-1123 demonstrated lower mitogenic potency relative to HI with respective $EC_{50}$ values of 80.5 nM and 12.9 nM. The mitogenic potency of T-1123 remained less than that of HI even after correcting for lower intrinsic IR-activation potency.

Example 12: In Vivo Potency

The potency of T-1123 and insulin lispro formulated in neutral buffer, preservative and tonicity agent was determined in a diabetic Lewis rats. T-1123 and insulin lispro (KP) were administered intravenously at 10 µg/300 g rat following a 2-h fast at the beginning of the light cycle. The resulting changes in blood glucose (BG) were measured over 5 h following dose administration using an EasyMax V glucometer. Time-action fitted BG curves are shown in (FIG. 10A). Potency in (FIG. 10B) is shown as the decrease in BG by mg/dl per µg administered and is calculated from the maximum drop in the PD curve. Measured potency indicates T-1123 is at least as potent as insulin lispro in the diabetic rat model.

Example 13: Formulations for Assessment of Fibril Formation in Polyphosphate Formulations Insulin analogues T-1123 (EA8, EA14, GA21, desB1, AB2, EB3, and EB29 relative to wild-type human insulin) and T-8602 (EA8, EA14, AA21, AB3, EB29, and EEGRR linker relative to wild-type human insulin; SEQ ID NO. 14) were evaluated for fibrillation lag time determined through an accelerated Thioflavin T (ThT) dye assay, described in Example 7. The samples were prepared for testing in 50 mM Tris buffer (at a pH of 7.4) containing 3.2 mg/mL m-Cresol, 16 mg/mL glycerin, and with or without 20 mM sodium triphosphate (triphosphate). See Table 18. In addition, Humalog® (Eli Lilly; with or without triphosphate) as well as Novolog® (Novo Nordisk, with or without triphosphate) were also tested for the lag time prior to onset of ThT-positive fibrillation. See Table 19.

TABLE 18

| | | | | | |
|---|---|---|---|---|---|
| Insulin Analogue Formulations for Fibrillation Assay | | | | | |
| T-Code | Mg + 2 (mM) | Glycerin (mg/mL) | m-Cresol (mg/mL) | Triphosphate (mM) | Tris (mM) |
| T-1123 | 0 | 16 | 3.2 | 0 | 50 |
| T-1123 | 0 | 16 | 3.2 | 20 | 50 |
| T-8602 | 0 | 16 | 3.2 | 20 | 50 |
| T-8602 | 0 | 16 | 3.2 | 0 | 50 |

TABLE 19

| | | | |
|---|---|---|---|
| Humalog ® and Novolog ® Formulations for Fibrillation Assay | | | |
| | Batch # | Expiration | Triphosphate (mM) |
| Humalog ® | D065900A | Apr.-22 | 0 |
| Humalog ® | D065900A | Apr.-22 | 20 |
| Novolog ® | JZFF071 | Sep.-21 | 0 |
| Novolog ® | JZFF071 | Sep.-21 | 20 |

Example 14: Accelerated Fibrillation Assay for Testing the Stability of Insulin Analogs Triplicate samples of insulin analogues (Humalog®, Novolog®, T-1123, and T-8602) were distributed into microplates in a synergy H1 spectrofluorometer (BioTek Instruments, Inc., Winooski, Vt.) at 40° C. under rapid agitation for up to seven (7) days and fibrils were detected using a thioflavin-T (ThT) fluorescence assay. ThT fluorescence measurements were performed every 20 min using excitation and emission wavelengths of 440 and 485 nm, respectively.

T-1123 formulated at U-500 in a base formulation of buffer, preservative and tonicity agent demonstrates fibrillation lag times that are unaffected by the addition of 20 mM sodium triphosphate (Table 20, FIG. 11A). This stands in marked contrast to Humalog® and Novolog®, which show sharp decreases in fibrillation lag time with the addition of 20 mM sodium triphosphate (Table 20). Also of note is that fibrillation lag times for T-1123 U-500 in base formulation with and without sodium triphosphate are > four times longer than commercial formulations of either Humalog® or Novolog® without sodium triphosphate. T-8602 formulated at U-100 in a base formulation of buffer, preservative and tonicity agent demonstrates fibrillation lag times that are unaffected by the addition of 20 mM sodium triphosphate (Table 20, FIG. 11B). This stands in marked contrast to Humalog® and Novolog®, which show sharp decreases in fibrillation lag time with the addition of 20 mM sodium triphosphate. Also of note is that fibrillation lag times for T-8602 U-100 in base formulation with and without sodium triphosphate are > twenty times longer than commercial formulations of either Humalog® or Novolog® without sodium triphosphate.

TABLE 20

Triphosphate effect on Fibrillation lag time

| TA | Mean lag time (hr) | SD (hr) | Comments |
|---|---|---|---|
| Humalog ® + triphosphate | 0.8 | 0.1 | |
| Humalog ® | 6.59 | 0.6 | |
| Novolog ® + triphosphate | 0.65 | 0.19 | |
| Novolog ® | 2.24 | 0.05 | |
| U-500 T-1123 in base formulation | 26.25 | 1.56 | |
| U-500 T-1123 in base formulation + triphosphate | 25.29 | 0.6 | |
| U-100 T-8602 in base formulation | 168+ | | Did not fibrillate in 168 hrs |
| U-100 T-8602 in base formulation + triphosphate | 168+ | | Did not fibrillate in 168 hrs |

FIG. 11C provides the results of further accelerated fibrillation assays. T-123 compositions were formulated as provided in Table 16 and tested against Humalog (n=3 in each instance). Each T-1123 formulation exhibited fibrillation lag times in excess of 168 days while Humalog exhibited a mean fibrillation lag time of 6.96 days.

Example 15: T-1123 Chemical Stability in Polyphosphate Formulations

T-1123 was formulated using a base formulation with and without TriPO4, as indicated in Table 21. To determine RS and HMWP, these formulations were heat stressed at 40° C. for 28 days. RS and HMWP were characterized as described in Example 8. After the incubation period, the presence of TriPO4 did not impact T-1123 chemical stability (FIG. 12) as both RS and HMWP remained similar upon the addition of 20 mM TriPO4.

TABLE 21

TriPO4 effect on T-1123 Base Formulations

| TriPO4 (mM) | RS (% Purity) | HMWP (% Purity) |
|---|---|---|
| 0 | 97.44 | 98.84 |
| 20 | 97.6 | 98.54 |

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

---

What is claimed:

1. A pharmaceutical composition comprising an effective amount of an insulin analogue comprising a modified A-chain polypeptide and a modified B-chain polypeptide, wherein the insulin analogue consists of the following modifications with respect to wild type human insulin: EA8, EA14, GA21, desB1, AB2, EB3, and EB29, and wherein the composition comprises one or more of ilo-prost, citrate, EDTA and a polyphosphate compound.

2. The pharmaceutical composition of claim 1, wherein the insulin analogue is monomeric or dimeric when formulated at U-500.

3. The pharmaceutical composition of claim 2, wherein the insulin analogue is formulated with a polyphosphate compound.

4. The pharmaceutical composition of claim 3, wherein the polyphosphate compound is one or more of a pyrophosphate, triphosphate, trimetaphosphate, and tetraphosphate.

5. The pharmaceutical composition of claim 1, wherein the insulin analogue is formulated with iloprost.

6. The pharmaceutical composition of claim 5, wherein the iloprost is present at a concentration of about 1 μg/mL to about 100 μg/mL.

7. The pharmaceutical composition of claim 5, wherein the insulin analogue is formulated with EDTA and citrate.

8. The pharmaceutical composition of claim 1, wherein the insulin analogue is formulated with less than 0.05 moles of zinc per mole of insulin.

9. The pharmaceutical composition of claim 1, wherein the insulin analogue is formulated with one or more of about 10 to about 100 mM Tris, about 0.1 mg/mL to about 10 mg/mL m-cresol, and about 0.1 mg/mL to about 25 mg/mL glycerin.

10. The pharmaceutical composition of claim 7, wherein the insulin analogue further comprises magnesium.

11. The pharmaceutical composition of claim 1, comprising iloprost at a concentration of about 5 μg/mL to about 50 μg/mL.

12. A method for treating a subject with diabetes or prediabetes, the method comprising administering to the subject pharmaceutically effective amount of an insulin analogue comprising a modified A-chain polypeptide and a modified B-chain polypeptide, wherein the insulin analogue consists of the following modifications with respect to wild type human insulin: EA8, EA14, GA21, desB1, AB2, EB3, and EB29, and wherein the composition comprises one or more of iloprost, citrate, EDTA and a polyphosphate compound.

13. The pharmaceutical composition of claim 1, comprising iloprost at a concentration of about 10 μg/mL to about 25 μg/mL.

\*   \*   \*   \*   \*